United States Patent
Kanthi et al.

(10) Patent No.: US 12,029,755 B2
(45) Date of Patent: Jul. 9, 2024

(54) CARBON MONOXIDE-BASED THERAPIES AND IMPLANTABLE DEVICES FOR THE TREATMENT OF VASCULAR DISEASE

(71) Applicant: THE REGENTS OF THE UNIVERSITY OF MICHIGAN, Ann Arbor, MI (US)

(72) Inventors: Yogendra Kanthi, Ann Arbor, MI (US); David J. Pinsky, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 17/535,080

(22) Filed: Nov. 24, 2021

(65) Prior Publication Data

US 2022/0160756 A1 May 26, 2022

Related U.S. Application Data

(63) Continuation of application No. 16/017,713, filed on Jun. 25, 2018, now abandoned.

(60) Provisional application No. 62/524,165, filed on Jun. 23, 2017, provisional application No. 62/524,174, filed on Jun. 23, 2017.

(51) Int. Cl.
| | |
|---|---|
| A61K 33/00 | (2006.01) |
| A61K 9/00 | (2006.01) |
| A61K 33/24 | (2019.01) |
| A61K 45/06 | (2006.01) |
| A61L 27/02 | (2006.01) |
| A61L 27/18 | (2006.01) |
| A61L 27/34 | (2006.01) |
| A61L 27/54 | (2006.01) |
| A61L 27/58 | (2006.01) |
| A61L 29/06 | (2006.01) |
| A61L 29/16 | (2006.01) |
| A61L 31/02 | (2006.01) |
| A61L 31/06 | (2006.01) |
| A61L 31/10 | (2006.01) |
| A61L 31/14 | (2006.01) |
| A61L 31/16 | (2006.01) |
| A61P 9/00 | (2006.01) |
| A61B 17/00 | (2006.01) |
| A61B 17/12 | (2006.01) |
| A61F 2/01 | (2006.01) |
| A61K 9/127 | (2006.01) |
| A61K 9/51 | (2006.01) |
| A61M 1/16 | (2006.01) |
| A61M 1/36 | (2006.01) |
| A61M 60/148 | (2021.01) |

(52) U.S. Cl.
CPC ............ *A61K 33/00* (2013.01); *A61K 9/0073* (2013.01); *A61K 33/24* (2013.01); *A61K 45/06* (2013.01); *A61L 27/025* (2013.01); *A61L 27/18* (2013.01); *A61L 27/34* (2013.01); *A61L 27/54* (2013.01); *A61L 27/58* (2013.01); *A61L 29/06* (2013.01); *A61L 29/16* (2013.01); *A61L 31/028* (2013.01); *A61L 31/06* (2013.01); *A61L 31/10* (2013.01); *A61L 31/148* (2013.01); *A61L 31/16* (2013.01); *A61P 9/00* (2018.01); *A61B 2017/00575* (2013.01); *A61B 2017/00893* (2013.01); *A61B 17/12022* (2013.01); *A61B 17/12122* (2013.01); *A61F 2/01* (2013.01); *A61K 9/0024* (2013.01); *A61K 9/127* (2013.01); *A61K 9/5153* (2013.01); *A61M 1/1698* (2013.01); *A61M 1/3666* (2013.01); *A61M 60/148* (2021.01); *A61M 2202/0233* (2013.01)

(58) Field of Classification Search
CPC . A61K 33/00; A61L 27/54; A61M 2202/0233
See application file for complete search history.

(56) References Cited

U.S. PATENT DOCUMENTS

| | | | |
|---|---|---|---|
| 2012/0045518 A1 | 2/2012 | Nielsen et al. | |
| 2014/0243581 A1* | 8/2014 | Otterbein | A61N 5/10 600/1 |
| 2018/0271086 A1* | 9/2018 | Meinel | A61M 35/30 |

FOREIGN PATENT DOCUMENTS

| | | | | |
|---|---|---|---|---|
| WO | WO-2015191616 A1 * | 12/2015 | | A61K 31/015 |

OTHER PUBLICATIONS

Kramkowski, K. et al. "Antithrombotic Properties of Water-Soluble Carbon Monoxide-Releasing Molecules" Arterioscler Thromb Vasc Biol, Sep. 2012, pp. 2149-2157 (Year: 2012).*

Weis et al., Heme oxygenase-1 contributes to an alternative macrophage activation profile induced by apoptotic cell supernatants, Mo/. Biol. Cell. 20:1280-8 (2009).

Welsh et al., Hemodynamic regulation of perivalvular endothelial gene expression prevents deep venous thrombosis, J Clin Invest. 2019; 129(12): 5489-5500.

Wenzel et al., Heme oxygenase-1 suppresses a pro-inflammatory phenotype in monocytes and determines endothelial function and arterial hypertension in mice and humans, Eur. Heart J. 36:3437-46 (2015).

(Continued)

*Primary Examiner* — Andrew S Rosenthal
(74) *Attorney, Agent, or Firm* — MARSHALL, GERSTEIN & BORUN LLP

(57) ABSTRACT

Disclosed herein are methods of treating venous thrombosis and vascular inflammation through administration of carbon monoxide and/or a carbon monoxide releasing molecule. Also disclosed herein are devices capable of releasing carbon monoxide for the purpose of treating microvascular, arterial and venous thromboembolism and/or inflammation.

11 Claims, 3 Drawing Sheets

(56) References Cited

OTHER PUBLICATIONS

Wiesel et al., Endotoxin-induced mortality is related to increased oxidative stress and end-organ dysfunction, not refractory hypotension, in heme oxygenase-1-deficient mice, Circulation. 102:3015-22 (2000).
LeWine, H. et al. (https://www.health.harvard.edu/blog/leg-clots-aka-deep-vein-thrombosis-an-immediate-and-long-term-health-hazard-201112143955/print/) Dec. 14, 2011, pp. 1-2 (Year: 2011).
Li et al., NF-kappaB transcription factor p50 critically regulates tissue factor in deep vein thrombosis, J. Biol. Chem. 284:4473-83 (2009).
Lindenblatt et al., Vascular heme oxygenase-1 induction suppresses microvascular thrombus formation in vivo, Arterioscler. Thromb. Vasc. Biol. 24:601-6 (2004).
Ling et al., Carbon Monoxide and Its Controlled Release: Therapeutic Application, Detection, and Development of Carbon Monoxide Releasing Molecules (CORMs), J Med. Chem., 61:2611-2635 (2018).
Machado, University of Illinois at Chicago. Carbon Monoxide therapy for severe pulmonary arterial hypertension. https://clinicaltrialsaov/ct2/show/NCT01523548 NLM Identfier NCT01523548 2012.
Magierowska et al., The Protective Role of Carbon Monoxide (CO) Produced by Heme Oxygenases and Derived from the CO-Releasing Molecule CORM-2 in the Pathogenesis of Stress-Induced Gastric Lesions: Evidence for Non-Involvement of Nitric Oxide (NO), Int. J. Mal. Sci., 17:442 (2016).
Maruyama et al., Carbon monoxide (CO)-releasing molecule-derived CO regulates tissue factor and plasminogen activator inhibitor type 1 in human endothelial cells, Thromb. Res., 130:3188-3193 (2012).
Mayr et al., Effects of carbon monoxide inhalation during experimental endotoxemia in humans, Am. J. Resoir. Grit. Care Med. 171:354-60 (2005).
Mcinturff et al., Mammalian target of rapamycin regulates neutrophil extracellular trap formation via induction of hypoxia-inducible factor 1 a, Blood. 120:3118-25 (2012).
Meng et al., In Vivo Role of Neutrophil Extracellular Traps in Antiphospholipid Antibody-Mediated Venous Thrombosis, Arthritis Rheumatol. 69:655-667 (2017).
Mishra et al., Carbon monoxide rescues ischemic lungs by interrupting MAPK-driven expression of early growth response 1 gene and its downstream target genes, Proc. Natl. Acad. Sci. USA. 103:5191-6 (2006).
Mizuguchi et al., CORM-3-derived CO modulates polymorphonuclear leukocyte migration across the vascular endothelium by reducing levels of cell surface-bound elastase, Am J Physiol Heart Gire Physiol, 297:H920-H929 (2009).
Morse et al., Inhaled CO in the treatment of acute lung injury, Am. J. Physiol. Lung. Cell. Mal. Physiol. 294:L642-3 (2008).
Mortellini et al., Emerging concepts on the anti-inflammatory actions of carbon monoxide-releasing molecules (CO-RMs), Med. Gas. Res. 2:28 (2012).
Motterlini et al., CORM-A1: a new pharmacologically active carbon monoxide-releasing molecule, FASEB J., 19(2):284-6 (2005).
Mukhopadhyay et al., Fibrinolysis and Inflammation in Venous Thrombus Resolution, Frontiers in Immunology, 10:1348 (2019).
Mustafa et al., Genetic variation in heme oxygenase 1 (HMOX1) and the risk of recurrent venous thromboembolism, J. Vase. Sur_q. 47:566-70 (2008).
Obi et al., Gram-Negative Pneumonia Alters Large-Vein Cell-Adhesion Molecule Profile and Potentiates Experimental Stasis Venous Thrombosis, J. Vase. Res. 53:186-195 (2016).
Osol, Remington's Pharmaceutical Sciences, Mack Publishing Company, Easton, PA (16th ed.1980).
Otterbein et al., Hemoglobin provides protection against lethal endotoxemia in rats: the role of heme oxygenase-1, Am. J. Respir. Cell Mal. Biol. 13:595-601 (1995).
Otterbein et al., Mechanism of hemoglobin-induced protection against endotoxemia in rats: a ferritin-independent pathway, Am. J. Physiol. 242:L268-75 (1997).
Patterson et al., Carbon monoxide-releasing molecule 3 inhibits myeloperoxidase (MPO) and protects against MPG-induced vascular endothelial cell activation/dysfunction, Free Radie. Biol. Med., 70:167-173 (2014).
Peng et al., Induction of heme oxygenase-1 expression inhibits platelet-dependent thrombosis, Antioxid. Redox. Siona/. 6:729-35 (2004).
Peterson et al.; "Predicting the carboxyhemoglobin levels resulting from carbon monoxide exposures;" Journal of Applied Physiology, vol. 39, No. 4, Oct. 1975, 633-638.
Pfeiffer, H. et al. "Sonogashira and "Click" reactions for the N-terminal and side-chain functionalization of peptides with [Mn(CO)3(tpm)]+-based CO releasing molecules (tpm=tris(pyrazolyl)methane)" Dalton Trans., 2009, 4292-4298 (Year: 2009).
Pinsky et al.; "Elucidation of the thromboregulatory role of CD39/ectoapyrase in the ischemic brain;" J Clin Invest. 2002;109(8):1031-1040.
Resch et al., Inhaled carbon monoxide increases retinal and choroidal blood flow in healthy humans, Invest. Ophthalmol. Vis. Sci. 46:4275-80 (2005).
Ridker et al., Rosuvastatin to prevent vascular events in men and women with elevated C-reactive protein, N. Eno/. J. Med. 359:2195-207 (2008).
Rodger et al., Management of suspected and confirmed recurrent venous thrombosis while on anticoaaulant therapy, Thrombosis Research. 180:105-9 (2019).
Rosen et al., Laser-induced Noninvasive Vascular Injury Models in Mice Generate Platelet- And Coaaulation-Dependent Thrombi, Am. J. Pathol. 158:1613-22 (2001).
Saha et al., Leukocytes and the natural history of deep vein thrombosis: current concepts and future directions, Arterioscler. Thromb. Vase. Biol. 31:506-12 (2011).
Schreiber et al. (2012) "T Cell Costimulation by TNFR Superfamily Vaccination (TNFRSF)4 and TNFRSF25 in the Context of Vaccination," J Immunol 189:3311-3318.
Schreiber, D. et al. (https://emedicine.medscape.com/article/1927155-overview) Dec. 28, 2015, pp. 1-6 (Year: 2015).
Schreiber, S., Heparin use in deep venous thrombosis, https://emedicine.medscape.com/article/1927155-overview, Dec. 28, 2015.
Song et al., Effects of exogenous carbon monoxide-releasing molecule 2 intervention in vitro on formation of human neutrophil extracellular traps stimulated by endotoxin/lipopolysaccharide and its mechanism, Zhonohua Shao Shano Za Zhi, 32(2):82-8 (2016).
Soni et al., Investigation into the mechanism(s) of antithrombotic effects of carbon monoxide releasing molecule-3 (CORM-3), Thromb. Res. 127:551-9 (2011).
Steiger et al., Localized delivery of carbon monoxide, Eur. J. Pharm. Biopharm., 118:3-12 (2017).
Suffredini, National Institutes of Health Clinical Center.Carbon monoxide to prevent lunginflammation. https://clinicaltrialsqov/ct2/show/NCT00094406 NLM Identifier NCT00094406 2004.
Tracz et al., Induction of heme oxygenase-1 is a beneficial response in a murine model of venousthrombosis, Am. J. Pathol. 173:1882-90 (2008).
True et al., Heme oxygenase-1 deficiency accelerates formation of arterial thrombosis through oxidative damage to the endothelium, which is rescued by inhaled carbon monoxide, Gire. Res. 101:893-901 (2007).
Turetz et al., Epidemiology, Pathophysiology, and Natural History of Pulmonary Embolism, Semin Intervent Radial, 35(2):92-98 (2018).
Urguhart et al., Carbon monoxide-releasing molecules modulate leukocyte-endothelial interactions under flow, J. Pharmacol. Exp. Ther. 321:656-62 (2007).
Van Es et al., Direct Oral anticoagulants compared with vitamin K antagonists for acute venous thromboembolism: evidence from phase 3 trials, Blood. 124:1968-75 (2014).
Villanueva et al., Netting neutrophils induce endothelial damage, infiltrate tissues, and expose immunostimulatory molecules in systemic lupus erythematosus, J. Immunol. 187:538-52 (2011).

(56) References Cited

OTHER PUBLICATIONS

VonBruhl et al., Monocytes, neutrophils, and platelets cooperate to initiate and propagate venous thrombosis in mice in vivo, J. Exp. Med. 209:819-35 (2012).
Vummaleti et al., Theoretical insights into the mechanism of carbon monoxide (CO) release from (2009).
Vummaleti et al., Theoretical Insights into the Mechanism of Carbon Monoxide (CO) Release from CO-Releasing Molecules, Chemistry, 18(30):9267-9275 (2012).
Wakefield et al., Call to action to prevent venous thromboembolism, J. Vasc. Sur. 49:1620-3 (2009).
Wang et al., Exogenous carbon monoxide inhibits neutrophil infiltration in LPS-induced sepsis by interfering with FPR1 via p38 MAPK but no GRK2, Oneotarget, 7(23):34250-34265 (2016).
Wang, Daping Hospital and the Research Institute of Surgery of the Third Military Medical University. Safety and adverse reaction study of neonatal to inhaled carbon monoxide. https://clinicaltrialsaov/ct2/show/NCT01818843. NLM Identifier: NCT01818843 2013.
"Carbon Monoxide (CO)" http://www.environment.gov.au/protection/publications/factsheet-carbon-monoxide-co; 2005, pp. 1-2 (Year: 2005).
Abeyranthna et al., Nonmetallic carbon nonoxide releasing molecules (CORMs), Org. Biomol. Chem., 15:8692 (2017).
Aksu et al., Inflammation-induced thrombosis: mechanisms, disease associations and management, Curr. Pharm. Des. 18:1478-93 (2012).
Anyanwu et al., Suppression of inflammatory cell trafficking and alveolar simplification by the heme oxygenase-1 product carbon monoxide, Am. J. Physiol. Lung Cell Mal. Physiol. 306:L749- 63 (2014).
Atkinson 116:4675-83 et al., (2010). Laser-induced endothelial cell activation supports fibrin formation, Blood. 116:4675-83 (2010).
Atkinson, B.T et al. "Laser-induced endothelial cell activation supports fibrin formation" Blood 116 (22), Nov. 25, 2010, pp. 4675-4683 (Year: 2010).
Barnes et al., Venous thromboembolism: diagnosis, treatment and the prevention of long-term complications, Rev. Vasc. Med. 2:136-42 (2014).
Barnes et al., Venous thromboembolism: predicting recurrence and the need for extended anticoaaulation, Vasc. Med. 20:143-52 (2015).
Bathoorn et al., Anti-inflammatory effects of inhaled carbon monoxide in patients with COPD: a pilot study, Eur. Respir. 30:1131-7 (2007).
Bean et al., Increased risk of venous thromboembolism is associated with genetic variation in heme oxvaenase-1 in Blacks, Thromb. Res. 130:942-7 (2012).
Bergmeier et al., Extracellular Matrix Proteins in Hemostasis and Thrombosis, Cold Spring Harb Perspect Biol, 4(2):a0051322012 (2012).
Braud et al., Carbon monoxide-induced metabolic switch in obese mice, JC/ Insight, 3(22):e123485 (2018).
Brill et al., Hypoxia, such as encountered at high altitude, promotes deep vein thrombosis in mice,J. Thromb. Haemost. 11:1773-5 (2013).
Brune et al., Inhibition of platelet aggregation by carbon monoxide is mediated by activation of guanylate cyclase, Mal. Pharmacol. 32:497-504 (1987).
Burgaud et al., Nitric-oxide releasing molecules: a new class of drugs with several major indications, Curr. Pharm. Des. 8:201-3 (2002).
Byrnes et al., Factor XIIIa-dependent retention of red blood cells in clots is mediated by fibrin alpha-chain crosslinkinq, Blood 126:1940-8 (2015).
Chen et al., Carbon monoxide rescues heme oxygenase-1-deficient mice from arterial thrombosis in allogeneic aortic transplantation, Am. J. Pathol. 175:422-9 (2009).
Cheng et al., Heme oxygenase 1 determines atherosclerotic lesion progression into a vulnerable plaque, Circulation. 119:3017-27 (2009).

Chiang et al., Inhaled carbon monoxide accelerates resolution of inflammation via unique proresolving mediator-heme oxvaenase-1 circuits, J. Immunol. 190:6378-88 (2013).
Chlopicki et al., Carbon monoxide released by CORM-3 inhibits human platelets by a mechanism independent of soluble guanylate cyclase, Cardiovascular Research, 71:393-401 (2006).
Chlopicki et al., Inhibition of platelet aggregation by carbon monoxide releasing molecules (CO-RMs): comparison with NO donors, Naunyn Schmiedebergs Arch Pharmacol., 385:641-650 (2012).
Choi, Weil Medical College of Cornell University. Safety Study of Inhaled Carbon Monoxide to Treat Acute Respiratory Distress Syndrome (ARDS). http://clinicaltrialsqov/NCT02425579. NLM Identifier: NCT02425579 2015.
Chou et al., Hematopoietic cell-derived microparticle tissue factor contributes to fibrin formation during thrombus propagation, Blood. 104:3190-7 (2004).
Chung et al., Carbon monoxide poisoning and risk of deep vein thrombosis and pulmonary embolism: a nationwide retrospective cohort study, J. Epidemiol. Community Health. 69:557-62 (2015).
Crowther et al., A comparison of two intensities of warfarin for the prevention of recurrent thrombosis in patients with the antiphospholipid antibody syndrome, N. Engl. J. Med. 349:1133-8 (2003).
De Stefano et al., High rate of recurrent venous thromboembolism in patients with myeloproliferative neoplasms and effect of prophylaxis with vitamin K antagonists, Leukemia. 30:2032-8 (2016).
Desch et al., Linkage analysis identifies a locus for plasma von Willebrand factor undetected by Qenome-wide association, Proc. Natl. Acad. Sci. USA. 110:588-93 (2013).
Diaz et al. Resolvin D2 reduces thrombus burden and attenuates inflammatory signaling pathways in a murine model of venous thrombosis. Arteriosclerosis, thrombosis, and vascular biology. 35(2015).
Diaz et al., Critical review of mouse models of venous thrombosis, Arterioscler. Thromb. Vasc. Biol. 32:556-62 (2012).
Diaz et al., Plasma DNA is Elevated in Patients with Deep Vein Thrombosis, J. Vasc. Surg. Venous Lymphat. Disord. 1 (2013).
Esmon, Inflammation and thrombosis, J. Thromb. Haemost. 1:1343-8 (2003).
Etulain et al., P-selectin promotes neutrophil extracellular trap formation in mice, Blood. 126:242-6 (2015).
Evans et al., Upregulation of hypoxia-inducible factor 1 alpha in local vein wall is associated with enhanced venous thrombus resolution, Thromb. Res. 128:346-51 (2011).
Ferrandiz et al., Treatment with a CO-releasing molecule (CORM-3) reduces joint inflammation and erosion in murine collagen-induced arthritis, Ann. Rheum. Dis. 67:1211-7 (2008).
Francis and Marder, Fibrinolytic Therapy for Venous Thrombosis, Progress in Cardiovascular Diseases, 34(3):193-204 (1991).
Fujita et al., Paradoxical rescue from ischemic lung injury by inhaled carbon monoxide driven by derepression of fibrinolysis, Nat. Med. 7:598-604 (2001).
Furchgott and Zawadzki, The obligatory role of endothelial cells in the relaxation of arterial smooth muscle by acetylcholine, Nature, 288:373-376 (1980).
Geddings et al., Tissue factor-positive tumor microvesicles activate platelets and enhance thrombosis in mice, J. Thromb. Haemost. 14:153-66 (2016).
Gomperts et al., The role of carbon monoxide and heme oxygenase in the prevention of sickle cell disease vaso-occlusive crises, Am. J. Hematol. 92:569-582 (2017).
Grosse et al., The economic burden of incident venous thromboembolism in the United States: A review of estimated attributable healthcare costs, Thromb. Res. 137:3-10 (2016).
Hamer et al., The PO2 in Venous Valve Pockets: Its Possible Bearing on Thrombogenesis, Br. J.Suro. 68:166-70 (1981).
Hayashi et al., Real-time analysis of platelet aggregation and procoagulant activity during thrombus formation in vivo. Eur. J. Physiol. 456:1239-1251 (2008).
Hyman et al., Self-regulation of inflammatory cell trafficking in mice by the leukocyte surface aovrase CD39, J. Clint. Invest. 119:1136-49 (2009).
Inoue et al., Carbon Monoxide-Releasing Molecule-401 Suppresses Polymorphonuclear Leukocyte Migratory Potential by Modulating F-Actin Dynamics, Am J Pathol, 187:1121-1133 (2017).

(56) References Cited

OTHER PUBLICATIONS

Izumi et al., Risk of venous thromboembolism after total knee arthroplasty in patients with rheumatoid arthritis, J. Rheumatol. 42:928-34 (2015).
Kahn et al., Post-thrombotic syndrome, functional disability and quality of life after upper extremity deep venous thrombosis in adults, Thromb. Haemost. 93:499-502 (2005).
Kerstjens, Groningen Research Institute for Asthma and COPD. Modification of chronic inflammation by inhaled carbon monoxide in patients with stable COPD. https://clinicaltrialsqov/ct2/show/NCT00122694 NLM Identifier NCT00122694 2006.
Koupenova et al.; "Thrombosis and platelets: an update;" European Heart Journal (2017) 38, 785-791.
Lawson et al.; "Monocytes and tissue factor promote thrombosis in a murine model of oxygen deprivation;" J Clin Invest. 1997;99(7):1729-1738.
Lee et al., Low-molecular-weight Heparin Versus a Coumarin for the Prevention of Recurrent Venous Thromboembolism in Patients With Cancer, N. Engl. J. Med. 349:146-53 (2003).

* cited by examiner (A)

(B)

Sham    Stasis    Stenosis

CARBON MONOXIDE-BASED THERAPIES AND IMPLANTABLE DEVICES FOR THE TREATMENT OF VASCULAR DISEASE

BACKGROUND OF THE INVENTION

Field of the Invention

The present disclosure relates to methods of treating arterial and venous thrombosis and vascular inflammation, as well as through administration of carbon monoxide and/or a carbon monoxide releasing molecule. Also disclosed herein are implantable devices that can release carbon monoxide for the purpose of treating microvascular arterial and venous thromboembolism and/or inflammation.

Description of Related Technology

Venous thromboembolism ("VTE"), which includes deep vein thrombosis ("DVT") and its potentially fatal complication pulmonary embolism ("PE"), is the third most common cardiovascular disease in the United States. VTE is estimated to affect over 900,000 patients each year, with up to 180,000 deaths annually in the U.S.[1] Thrombus developing in the deep veins of the legs and pelvis (DVT) are a considerable health burden. VTE has an estimated cost of $10 billion/year,[37] with patients suffering from post-thrombotic syndrome and persistently impaired quality of life.[38] Current management guidelines are based on anticoagulants targeting the coagulation cascade which are not fully effective, and limited by significant bleeding complications.[2,3] Patients experiencing initial VTE have a 25% incidence of recurrent VTE, and up to 30% suffer the long-term complications of post-thrombotic syndrome.[2,3] Studies have identified genetic and environmental risk factors for VTE including immobility (stasis) and systemic local inflammation. Platelets, red blood cells ("RBCs") and leukocytes, in particular neutrophils and macrophages, and also other immune cells, have been implicated in venous thrombogenesis.[4-8]

Inflammation is a fundamental immune response to protect blood vessels against injury. When combined with hypoxia-induced pathways and turbulent flow in venous valve pockets and at arterial bend and branch points, inflammation remains unchecked and can be maladaptive, triggering a variety of acute and chronic processes including microvascular thrombosis, venous thrombosis, valvular and vascular calcification, and even atherosclerosis and plaque rupture.[7,39-41] Growing evidence points toward a central role of inflammation in these processes, yet there is a knowledge gap in the molecular processes at the intersection of inflammation and thrombosis.[7,20-23] Thus, there is limited understanding of the molecular processes at the nexus of thrombosis and sterile inflammation where microvascular thrombosis, DVT, atherosclerosis, and valvular deterioration or stenosis frequently occur.[7]

Recent studies have shown the importance of innate immune system activation and release of procoagulant factors in venous thrombogenesis.[5-8,42-43] Under conditions known to trigger venous thrombosis, activated neutrophils undergo programmed apoptosis and release a web of extruded chromatin (neutrophil extracellular trap, "NET") that serves as a scaffold in thrombogenesis. NET formation ("NETosis") has been implicated in human and mouse thrombogenesis, evidenced by thrombi being "decorated" by neutrophils at the clot's leading edge or vessel wall:thrombus interface, suggesting a role in early thrombus formation and/or propagation.[5,8,44] Another procoagulant molecule, tissue factor has been identified as a potentiating factor in DVT, but the sources of tissue factor are varied (smooth muscle cells, fibroblasts, macrophages, activated endothelium), and an understanding of proximate regulators of thrombo-inflammation will be important in designing future therapeutics.[45] Current treatment strategies in venous thrombosis have focused on anticoagulation, precisely inhibiting the classic components of the coagulation cascade without targeting the coexisting inflammatory pathways. With diverse cell types involved in venous thrombosis, central regulators of hemo-endothelial activation represent promising targets for exploration.

One molecular factor at the intersection of inflammation and hemostasis is the enzyme heme oxygenase-1 ("HO-1"). Heme oxygenase-1, a critical modulator of host defense and inflammation, is an enzyme that catalyzes the degradation of pro-oxidant heme into anti-thromboinflammatory carbon monoxide ("CO"), biliverdin and iron. HO-1 has been found to be a regulator of vascular thrombo-inflammatory processes.[12,18,19] HO-1 expression is strongly induced in vascular tissue under stress conditions, accelerating heme catabolism into iron and the anti-oxidants CO and biliverdin.[18,19] There is growing awareness of the important roles for HO-1 in a number of disease processes including arterial atherosclerosis and thrombosis.[9-12]

Further, the discovery of genetic predispositions to venous thrombosis has significantly informed the approach to prevention of incident and recurrent VTE. Polymorphisms in the gene encoding HO-1 have been associated with an increased risk for VTE,[13-14, 15,16] although the cellular and molecular mechanism(s) by which this occurs remain largely unknown.[7,12]

Although the beneficial roles of HO-1 are not completely understood, many of these cytoprotective and anti-thromboinflammatory effects are related to the degradation of heme into its end-products-carbon monoxide, biliverdin and iron ($Fe^{2+}$), and specifically its generation of carbon monoxide.[13,14,18,19,24-27]

CO, an odorless gas commonly viewed as an environmental poison, plays a central role in suppressing inflammation vascular permeability, platelet activation, and chemically-induced arterial thrombosis by affecting fibrinolysis.[15-17] Studies have shown that CO has anti-inflammatory, anti-proliferative, and anti-apoptotic effects when the concentrations of CO in carrier gas (air) ranges from 10 to 250 ppm. In particular, CO is known to reduce neutrophil migration, enhance macrophage scavenging of apoptotic polymorphonuclear leukocyte ("PMNs"), and accelerate resolution of acute inflammation.[28] CO may induce specialized pro-resolving mediators, which play important roles in resolution of sterile inflammation including venous thrombo-inflammation.[28,29] Interestingly, CO can, in turn, enhance HO-1 expression, propagating a positive feedback loop whereby inflammation is not left unchecked.[28] Importantly, inhaled CO has been studied as a therapeutic agent in human disease with two successfully completed phase I trials, and at three phase 2 trials in pulmonary disease which have continued approval by their respective data safety monitoring boards.[30-36]

A cytoprotective effect by CO in pulmonary microvascular ischemic stress was previously identified.[19] This protection occurred via inhibition of ERK1/2-driven Egr-1 expression, and suppression of downstream thrombo-inflammatory mediators. In addition, another unique mechanism by which CO exerts its anti-thrombotic effect in hypoxic conditions has been elucidated by activating soluble guanylate cyclase, inhibiting plasminogen activator inhibitor-1 induction and preventing buildup of fibrin.[18] Additional studies have demonstrated direct inhibitory effects of carbon monoxide on platelet aggregation.[24] Attempts to harness the therapeutic potential of carbon monoxide have centered around low-dose inhaled CO to treat pulmonary disorders. Several phase I and phase II clinical trials with inhaled carbon monoxide have been completed or are underway, demonstrating the feasibility of inhaled CO as a therapeutic agent.[30-36] Synthetic carbon monoxide-releasing molecules ("CORM") have been utilized in vitro and in vivo to induce CO.[55,56] Of the water-soluble CORMs which can be given by intraperitoneal or intravenous injection for more reliable delivery, CORM-3 has shown potent effects on inflammation in pre-clinical studies.[56]

CO has been used to treat arterial thrombosis as well as chemically-induced and laser-induced venous thrombosis.[57] However, CO has so far been unsuccessful in treating physiological venous thrombosis, such as venous thrombosis which occurs in a cytokine-rich milieu, in the setting of cancer or inherited or acquired thrombophilias, or which occurs under conditions of low oxygen, immobilization, and/or limited flow.[61]

Thus, a need exists for developing methods of treating physiological venous thrombosis and providing devices capable of treating arterial and venous thromboembolism and/or inflammation.

SUMMARY OF THE INVENTION

In one aspect, provided herein is a method of treating physiological venous thrombosis in a patient in need thereof comprising administering to the patient a therapeutically effective amount of: (i) carbon monoxide ("CO"), (ii) a carbon monoxide releasing molecule or pharmaceutically acceptable salt thereof ("CORM"), or (iii) both CO and a CORM, or pharmaceutically acceptable salt thereof.

In another aspect, provided herein is a method of treating a disease or condition associated with low or no blood flow, sickle cell disease, or a combination thereof, comprising administering to a patient in need thereof a therapeutically effective amount of: (i) CO, (ii) a CORM or pharmaceutically acceptable salt thereof, or (iii) both CO and a CORM or pharmaceutically acceptable salt thereof, wherein the disease or condition is selected from primary or recurrent venous thrombophlebitis, arteriovenous shunt failure (e.g., thrombus, inflammation, neointimal hyperplasia), stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation (e.g, venous and arterial), atrial fibrillation, atrial flutter-related thrombus, endovascular (including endovenous) heat-induced thrombus (as might be seen with endovenous ablation), valve thrombosis (e.g., native, artificial, bioprosthetic), catheter thrombosis, thrombosis associated with tissue ablation procedures, implantable lead-associated thrombosis (e.g., catheter-associated, pacemaker, graft- or stent-related, lead-associated thrombosis, or thrombosis associated with other implanted cardiac or endovascular material), and a combination thereof.

In some embodiments, the patient is administered CO. In various embodiments, the patient is administered a CORM or pharmaceutically acceptable salt thereof. In some cases, the patient is administered both CO and a CORM or pharmaceutically acceptable salt thereof. In some embodiments, the CORM is a metal-containing CORM. The metal-containing CORM can be tricarbonyldichlororuthenium (II) dimer ("CORM-2"), tricarbonylchloro(glycinato)ruthenium (II) ("CORM-3"), [Me$_4$N][Mn(CO)$_4$(thioacetate)$_2$] ("CORM-371"), dimanganese decacarbonyl, or iron pentacarbonyl. For example, the CORM can be CORM-3. In various embodiments, the CORM is a nonmetal-containing CORM. For example, the CORM can be dicholormethane or sodium boranocarbonate ("CORM-A1"). In some cases, the CORM is coupled to a targeted delivery vector.

In various embodiments, the CO and/or CORM (or pharmaceutically acceptable salt thereof) can be administered by inhalation, infusion, injection, enterically, intraperitoneally, or topically. In some embodiments, the CO and/or CORM (or pharmaceutically acceptable salt thereof) is administered by inhalation. In various embodiments, the CO and/or CORM (or pharmaceutically acceptable salt thereof) is administered by infusion. In some cases, the CO and/or CORM (or pharmaceutically acceptable salt thereof) is administered by injection. In some cases, the CO and/or CORM (or pharmaceutically acceptable salt thereof) is administered enterically. In various embodiments, the CO and/or CORM (or pharmaceutically acceptable salt thereof) is administered topically. In some embodiments, the CORM is encased in a nanoparticle or nanodisk. In some cases, the nanoparticle or nanodisk comprises biodegradable polylactic acid ("PLA"), biodegradable polyglycolic acid ("PGA"), biodegradable poly(lactic-co-glycolic acid) ("PGLA"), or a combination thereof. In various cases, the nanoparticle is a liposome.

In another aspect, provided herein is an implantable device capable of releasing carbon monoxide for the purpose of treating arterial and venous thromboembolism and/or inflammation. The device described herein comprises a surface that is coupled to: (i) CO, (ii) a CORM, or (iii) both CO and a CORM. The device described herein can be selected from the group consisting of a vascular stent, an intracardiac occlusion device, an intracardiac valve, an implantable ventricular assist device, a vascular filter, a vascular catheter or lead, a cardiopulmonary bypass circuit, a extracorporeal membrane oxygenation circuit, or an implantable graft at the blood interface.

In some embodiments, the surface of the device is coupled to CO. In various embodiments, the surface of the device is coupled to a CORM. In some cases, the surface of the device is coupled to both CO and a CORM. In some embodiments, the CORM is a metal-containing CORM. The metal-containing CORM can be tricarbonyldichlororuthenium (II) dimer ("CORM-2"), tricarbonylchloro(glycinato)ruthenium (II) ("CORM-3"), [Me$_4$N][Mn(CO)$_4$(thioacetate)$_2$] ("CORM-371"), dimanganese decacarbonyl, or iron pentacarbonyl. For example, the CORM can be CORM-3. In various embodiments, the CORM is a nonmetal-containing CORM. For example, the CORM can be dicholormethane or sodium boranocarbonate ("CORM-A1"). In some cases, the CORM is coupled to a targeted delivery vector.

In some cases, the surface of the device is coated with the CO and/or CORM. In various cases, the surface of the device is impregnated with the CO and/or CORM. In some embodiments, the surface of the device is layered with the CO and/or CORM. In various embodiments, the surface of the device is etched with the CO and/or CORM. In some cases, the surface of the device is engrafted with the CO and/or CORM. In various cases, the surface of the device is covalently bound to the CO and/or CORM. In some cases, the surface of the device comprises polylactic acid ("PLA"), polyglycolic acid ("PGA"), poly(lactic-co-glycolic acid) ("PGLA"), or a combination thereof. In various cases, the device itself is composed of polylactic acid ("PLA"), polyglycolic acid ("PGA"), poly(lactic-co-glycolic acid) ("PGLA"), or a combination thereof. In some embodiments, the CORM is coupled to a targeted delivery vector.

In various embodiments, the CORM is encased in a nanoparticle or nanodisk. In some cases, the nanoparticle or nanodisk comprises biodegradable polylactic acid ("PLA"), biodegradable polyglycolic acid ("PGA"), biodegradable poly(lactic-co-glycolic acid) ("PGLA"), or a combination thereof. In various cases, the nanoparticle is a liposome.

In yet another aspect, provided herein is a method of treating a disease or condition associated with low or no blood flow, sickle cell disease, or a combination thereof in a patient in need thereof, comprising implanting the implantable device described herein in the patent in need thereof. The disease or condition can be selected form venous thromboembolism ("VTE"), native or artificial thrombosis, primary or recurrent thrombophlebitis, arteriovenous shunt failure, stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation, atrial fibrillation, atrial flutter-related thrombus, endovascular heat-induced thrombus, valve thrombosis, catheter thrombosis, thrombosis associated with tissue ablation procedures, implantable lead-associated thrombosis, and a combination thereof. In some embodiments, the disease or condition is venous thromboembolism ("VTE"). In various embodiments, the disease or condition is vascular inflammation.

Any of the methods described herein can further comprise administering to the patient one or more therapeutic agents. The one or more therapeutic agents can include nitric oxide or a compound that release nitric oxide, oxygen, an anticoagulant, an anti-inflammatory agent, a protease activated receptor ("PAR") inhibitor (e.g., vorapaxar), a thienopyridine, a lipoxygenase-derived platelet inhibitor, a cell adhesion molecule inhibitor, or a combination thereof. In some cases, the therapeutic agent comprises nitric oxide or a compound that releases nitric oxide. Suitable compounds that release nitric oxide include, for example, SIN-1, NCX-4016, NCX-701, nitroglycerin, sodium nitroprusside, and a combination thereof. In various cases, the therapeutic agent comprises oxygen. In various embodiments, the therapeutic agent comprises an anticoagulant. The anticoagulant can be selected from the group consisting of a coumarin, an indandione, a factor Xa inhibitor, factor XI inhibitor, factor XII inhibitor, factor XIII inhibitor, a heparin, a thrombin inhibitor, and a combination thereof. In some embodiments, the anticoagulant is warfarin. In various embodiments, the factor Xa inhibitor is fondaparinux, rivaroxaban, apixaban, edoxaban, otamixaban, letaxaban, eribaxaban, darexaban, or a combination thereof. In some cases, the heparin is dalteparin, tinzaparin, enoxaparin, heparin, danaparoid, or a combination thereof. In various cases, the thrombin inhibitor is bivalirudin, dabigatran, argatroban, desirudin, lepirudin, or a combination thereof. In some embodiments, the therapeutic agent comprises an anti-inflammatory, such as acetylsalicylic acid. In various embodiments, the therapeutic agent comprises a PAR inhibitor (e.g., vorapaxar). In some cases, the therapeutic agent comprises a thienopyridine (e.g., clopidogrel, prasugrel, or ticlopidine). In various embodiments, the therapeutic agent comprises a lipoxygenase-derived platelet inhibitor.

Further aspects and advantages will be apparent to those of ordinary skill in the art from a review of the following detailed description, taken in conjunction with the drawings.

While the compounds and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE INVENTION

Figure 1:
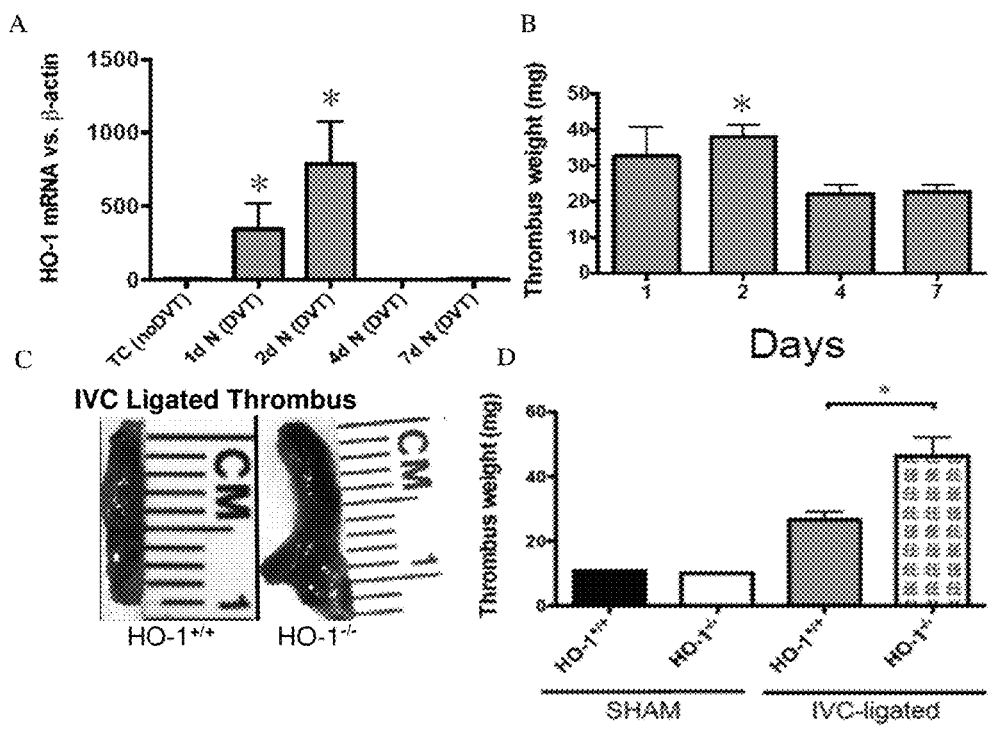
FIG. 1 depicts the central role of HO-1 in mitigating venous stasis thrombogenesis. A. HO-1 mRNA induction in inferior vena cava ("IVC") of wild type ("WT") mice following IVC ligation; B. Temporal pattern of thrombus burden in WT mice peaks 2 d following IVC ligation; C-D. Effect of HO-1 deficiency on venous thrombogenesis 2 d after IVC ligation. "TC"=true controls, "N"=normoxia; n=8-20 per group. *$P<0.05$.

Described herein are methods for treating physiological venous thrombosis and vascular inflammation in a patient by administering CO or a CORM to the patient. Further described herein are implantable devices capable of releasing a therapeutically effective amount of CO for the purpose of treating arterial and venous thromboembolism and/or inflammation. The methods and devices described herein are safe and easily translatable, and can temper venous thrombo-inflammation to prevent immediate and long-term complications.

It has been found that HO-1 and its end-product, CO, are novel mitigators of venous thrombo-inflammation. Therefore, inhaled CO and/or CORM can serve as therapeutic agents to mitigate venous thrombosis and vein wall inflammation. These findings are contrary to what the skilled person understood from the art that CO and/or CORMs were ineffective in mitigating physiological venous thrombosis.[1]

Definitions

As used herein the terms "treating", "treat" or "treatment" and the like include preventative (e.g., prophylactic) and palliative treatment.

As used herein, "physiological venous thrombosis" refers to venous thrombosis that did not occur due to an artificial cause, such as chemical-induced or laser-induced thrombosis. In physiological venous thrombosis, the veins of a patient can exhibit low or no blood flow.

As used herein, the term "therapeutically effective amount" means an amount of CO and/or CORM that ameliorates, attenuates or eliminates one or more symptoms of a disease or condition, such as venous thrombosis or inflammation, or prevents or delays the onset of one of more symptoms of the disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans).

As used herein, a "carbon monoxide releasing molecule" or "CORM" refers to a metal or nonmetal compound, or pharmaceutically acceptable salt thereof, that can release CO. In some embodiments, a CORM can deliver controlled quantities of CO gas to cells and tissues. The CORM can release carbon monoxide spontaneously, or by contacting, for example, a suitable solvent or medium, such as an aqueous physiological fluid (e.g., blood or lymph), or an aqueous physiological cellular material, such as a tissue, organ, or cell. A CORM also can release carbon monoxide by irradiation. For example, the CORM can be irradiated either prior to administration to produce a solution of dissolved CO, or in situ after administration.

In the methods and devices described herein, the CORMs can include those having a transition metal or metalloid and one or more carbonyl ligand(s). The transition metal or metalloid, for example, can be ruthenium, iron, manganese, cobalt, nickel, molybdenum, rhodium, or boron. The carbonyl ligand(s) can be coordinated to the metal center, or bonded to other groups by ionic or covalent bonds. The CORMs described herein can also include additional ligands that may modulate a particular property of the CORM, such as, for example, the rate of releasing carbon monoxide, solubility, hydrophobicity, stability, or electrochemical potential. The additional ligands can be, for example, halides, sulfoxides, natural and synthetic amino acids, aromatics, carboxylates, ethers, alcohols, or nitriles.

Suitable CORMs for use with the methods and devices described herein include tricarbonyldichlororuthenium (II) dimer ("CORM-2"), tricarbonylchloro(glycinato)ruthenium (II) ("CORM-3"), sodium boranocarbonate ("CORM-A1"), [Me$_4$N][Mn(CO)$_4$(thioacetate)$_2$]("CORM-371"), dimanganese decacarbonyl, iron pentacarbonyl, and silacarboxylic acids, some of which are pictured below.

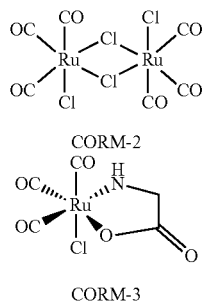

CORM-2

CORM-3

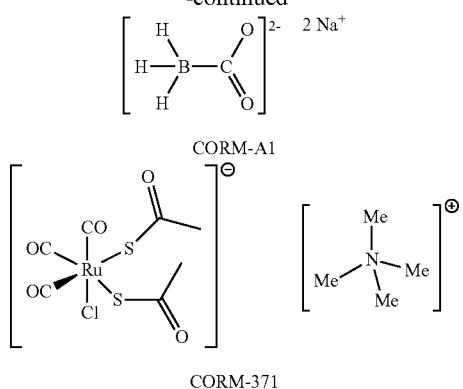

CORM-A1

CORM-371

Other suitable CORMs include compounds that metabolize into CO in vivo, such as methylene chloride, and any CORM described in, for example, Motterlini et al., Medicinal Gas Research 2(28):1-12 (2012), Vummaleti et al., Chemistry 18(30):9267-9275 (2012), or PCT publication no. WO 2015/191616, which is incorporated herein by reference. In some embodiments, the CORM used in the methods described herein is a water-soluble CORM, such as CORM-3.

As used herein, the term "targeted delivery vector" refers to any moiety that targets a particular cell type. A targeted delivery vector includes, but is not limited to, a ligand, carbohydrate, antibody, protein, enzyme, nucleic acid, drug or combinations thereof. Cell-targeting moieties can target a cell by interacting with, or binding to, cell-surface receptors or other molecules on the cell surface. Cell-targeting moieties can target a cell by interacting with, or binding to, disease-specific biomarkers. Such biomarkers belong to any condition or disease, and include, but are not limited to, biological molecules such as proteins, peptides, lipids, RNAs, DNA and variations and modifications thereof. Biomarkers may be circulating or localized. In some embodiments, the targeting molecule targets a disease-associated biomarker. In some embodiments, the biomarker is a cancer-associated biomarker. In some embodiments, the biomarker is prostate-specific membrane antigen ("PSMA").

Methods

Provided herein are methods of treating physiological venous thrombosis in a patient in need thereof comprising administering to the patient a therapeutically effective amount of: (i) carbon monoxide ("CO"), (ii) a carbon monoxide releasing molecule ("CORM"), as described supra, or a pharmaceutically acceptable salt thereof, or (iii) both CO and a CORM or pharmaceutically acceptable salt thereof.

In some embodiments, the patient is administered CO. In various embodiments, the patient is administered a CORM or pharmaceutically acceptable salt thereof. In some cases, the patient is administered both CO and a CORM (or pharmaceutically acceptable salt thereof). In some embodiments, the CORM is a metal-containing CORM. Suitable metal-containing CORMs can be tricarbonyldichlororuthenium (II) dimer ("CORM-2"), tricarbonylchloro(glycinato)ruthenium (II) ("CORM-3"), [Me$_4$N][Mn(CO)$_4$(thioacetate)$_2$]("CORM-371"), dimanganese decacarbonyl, iron pentacarbonyl, or a combination thereof.

For example, the CORM can be CORM-3. In various embodiments, the CORM is a nonmetal-containing CORM. Suitable nonmetal-containing CORMs can be dicholormethane or sodium boranocarbonate ("CORM-A1"). In some cases, the CORM is coupled to a targeted delivery vector, as described supra.

In some embodiments, the CORM can be encased in a nanoparticle or nanodisk.

In some cases, the nanoparticle or nanodisk comprises biodegradable polylactic acid ("PLA"), biodegradable polyglycolic acid ("PGA"), biodegradable poly(lactic-co-glycolic acid) ("PGLA"), or a combination thereof. In various cases, the nanoparticle is a liposome. The liposome can be composed of any of the common agents typically used to prepare liposomes suitable for pharmaceutical administration, such as, for example, cell membrane fragments or synthetic lipids. Suitable synthetic lipids include, for example, cationic lipids, phospholipids, triglyerides, sterols such as cholesterol, and combinations thereof. Methods for encasing pharmaceutical agents in nanoparticles and nanodisks are well known to those skilled in the art, and any suitable method can be used to encase the CORM described herein in a nanoparticle or nanodisk. In some cases, the liposome comprises a targeted delivery vector, as described supra.

In various embodiments, the CO and/or CORM (or pharmaceutically acceptable salt thereof) can be administered by inhalation, infusion, injection, enterically, intraperitoneally, or topically. In some embodiments, the CO and/or CORM (or pharmaceutically acceptable salt thereof) is administered by inhalation. In various embodiments, the CO and/or CORM (or pharmaceutically acceptable salt thereof) is administered by infusion. In some cases, the CO and/or CORM (or pharmaceutically acceptable salt thereof) is administered by injection. In various cases, the CO and/or CORM (or pharmaceutically acceptable salt thereof) is administered enterically. In some embodiments, the CO and/or CORM (or pharmaceutically acceptable salt thereof) is administered topically.

Also provided herein are methods of treating a disease or condition associated with low or no blood flow, sickle cell disease, or a combination thereof, in a patient in need thereof comprising administering to the patient a therapeutically effective amount of: (i) CO, (ii) a CORM or pharmaceutically acceptable salt thereof, or (iii) both CO and a CORM (or pharmaceutically acceptable salt thereof), wherein the disease or condition associated with low or no blood flow is selected from primary or recurrent venous thrombophlebitis, arteriovenous shunt failure (e.g., thrombus, inflammation, neointimal hyperplasia), stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation (e.g., venous and arterial), atrial fibrillation, atrial flutter-related thrombus, endovascular (including endovenous) heat-induced thrombus (as might be seen with endovenous ablation), valve thrombosis (e.g., native, artificial, bioprosthetic), catheter thrombosis, thrombosis associated with tissue ablation procedures, implantable lead-associated thrombosis (e.g., catheter-associated, pacemaker, graft- or stent-related, lead-associated thrombosis, or thrombosis associated with other implanted cardiac or endovascular material), and a combination thereof. In some embodiments, the disease or condition is a vascular occlusive and/or inflammatory complication.[63] In some cases, the vascular occlusive and/or inflammatory complication is sickle cell disease. In some cases, the sickle cell disease is sickle cell crises. In various cases, the sickle cell disease is associated with a neurologic outcome. In some embodiments, the sickle cell disease is associated with a non-neurologic outcome.

Further provided herein are methods of treating a disease or condition associated with low or no blood flow, sickle cell disease, or both, in a patient in need thereof comprising implanting the device described infra in the patient. In some embodiments, the disease or condition is selected from venous thromboembolism ("VTE"), native or artificial thrombosis, primary or recurrent thrombophlebitis, arteriovenous shunt failure, stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation, atrial fibrillation, atrial flutter-related thrombus, endovascular heat-induced thrombus, valve thrombosis, catheter thrombosis, thrombosis associated with tissue ablation procedures, implantable lead-associated thrombosis, and a combination thereof. In some embodiments, the disease or condition is venous thromboembolism. In various embodiments, the disease or condition is vascular inflammation. In some cases, the disease or condition is native or artificial thrombosis. In some embodiments, the disease or condition is a vascular occlusive and/or inflammatory complication.[63] In some cases, the vascular occlusive and/or inflammatory complication is sickle cell disease. In some cases, the sickle cell disease is sickle cell crises. In various cases, the sickle cell disease is associated with a neurologic outcome. In some embodiments, the sickle cell disease is associated with a non-neurologic outcome.

Any of the methods described herein can further comprise administering to the patient one or more therapeutic agents (e.g., targeting antibody, non-targeting antibody, small molecule, or biologic drug. In some embodiments, such combination therapy provides a synergistic effect. Suitable therapeutic agents can include nitric oxide or a compound that releases nitric oxide, oxygen, an anticoagulant, an anti-inflammatory agent, a protease activated receptor ("PAR") inhibitor (e.g., vorapaxar), a thienopyridine, a lipoxygenase-derived platelet inhibitor, a cell adhesion molecule inhibitor, and combinations thereof. In some cases, therapeutic agent comprises nitric oxide or a compound that releases nitric oxide. Suitable compounds that release nitric oxide include, for example, SIN-1, NCX-4016, NCX-701, nitroglycerin, sodium nitroprusside, and a combination thereof.[62] When the CO and/or CORM is paired with NO and/or a NO releasing molecule, therapeutic synergy results. In various cases, the therapeutic agent comprises oxygen. In various embodiments, the therapeutic agent comprises an anticoagulant. The anticoagulant can be selected from the group consisting of a coumarin, an indandione, a factor Xa inhibitor, factor XI inhibitor, factor XII inhibitor, factor XIII inhibitor, a heparin, a thrombin inhibitor, and a combination thereof. In some embodiments, the anticoagulant is warfarin. In various embodiments, the factor Xa inhibitor is fondaparinux, rivaroxaban, apixaban, edoxaban, otamixaban, letaxaban, eribaxaban, darexaban, or a combination thereof. In some cases, the heparin is dalteparin, tinzaparin, enoxaparin, heparin, danaparoid, or a combination thereof. In various cases, the thrombin inhibitor is bivalirudin, dabigatran, argatroban, desirudin, lepirudin, or a combination thereof. In some embodiments, the therapeutic agent comprises an anti-inflammatory agent, such as acetylsalicylic acid. In various embodiments, the therapeutic agent comprises a PAR inhibitor (e.g., vorapaxar). In some cases, the therapeutic agent comprises a thienopyridine (e.g., clopidogrel, prasugrel, or ticlopidine). In various embodiments, the therapeutic agent comprises a lipoxygenase-derived platelet inhibitor. In some embodiments when the CORM is encased in a nanoparticle or nanodisk, the one or more therapeutic agent is also encased within the liposome. In various embodiments when the CORM is encased in a nanoparticle or nanodisk, the one or more therapeutic agents is not encased in the nanoparticle or nanodisk with the CORM.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions might be different forms. For example, one or more compound may be delivered via a tablet, while another is administered via injection or orally as a syrup. All combinations, delivery methods and administration sequences are contemplated.

Devices

The disclosure further provides implantable devices comprising a surface coupled to: (i) CO, (ii) a CORM, or (iii) both CO and a CORM. The devices described herein release CO to treat diseases.

In some embodiments, CO is coupled to the surface of the device. In various embodiments, a CORM is coupled to the surface of the device. In some cases, both CO and a CORM is coupled to the surface of the device.

In some embodiments, the CORM is a metal-containing CORM. Suitable metal-containing CORMs can be tricarbonyldichlororuthenium (II) dimer ("CORM-2"), tricarbonylchloro(glycinato)ruthenium (II) ("CORM-3"), [Me$_4$N][Mn(CO)$_4$(thioacetate)$_2$]("CORM-371"), dimanganese decacarbonyl, iron pentacarbonyl, or a combination thereof. For example, the CORM can be CORM-3. In various embodiments, the CORM is a nonmetal-containing CORM. Suitable nonmetal-containing CORMs can be dicholormethane or sodium boranocarbonate ("CORM-A1"). In some cases, the CORM itself is coupled to a targeted delivery vector, as described supra.

In some embodiments, the CORM can be encased in a nanoparticle or nanodisk, as described supra.

The CO and/or CORM can be coupled to the surface of the device by any means known to those skilled in the art. Examples of coupling the CO and/or CORM to the surface of the device include coating the surface with the CO and/or CORM, impregnating the surface with the CO and/or CORM, layering the surface with the CO and/or CORM, etching the surface with the CO and/or CORM, engrafting the surface with the CO and/or CORM, covalently bonding the surface to the CO and/or CORM, and a combination thereof. Thus, in some embodiments, the surface of the device is coated with the CO and/or CORM. In various embodiments, the surface of the device is impregnated with the CO and/or CORM. In some cases, the surface of the device is layered with the CO and/or CORM. In various cases, the surface of the device is engrafted with the CO and/or CORM. In some embodiments, the surface of the device is covalently bound to the CO and/or CORM.

The CORM can be loosely coupled to the surface (e.g., impregnating) of the device or tightly coupled in the surface of the device (e.g., via covalent bonding). In some embodiments, the CORM is coupled to the device surface by pre-implantation device immersion, such as by dipping the device in a sterile CORM prior to implantation of the device. Coupling the CORM to the device just prior to implantation can prevent CO from prematurely releasing from the device, and can also prevent any shelf-life issues with the CORM. In various embodiments, the CORM is coupled to the device after the device has been implanted via local delivery of the CORM to the implanted device or via ligand-targeting. In some cases, local delivery of the CORM to an implanted device includes using a catheter to inject/coat the device surface. This post-implantation device coating can occur immediately after the device has been implanted or years later. For example, an implanted device that had been coupled to a CORM before implantation (e.g., into the interatrial septum, to close off an atrial septal defect—a hole between the top two chambers of the heart, generally a congenital lesion) can be re-coupled with the CORM using post-implantation coupling at a later period in time (e.g., 6 months, 1 year, 2 years later) to pacify the surface of the old implanted device (e.g., to keep stroke risk low).

In some cases, the surface of the device comprises polylactic acid ("PLA"), polyglycolic acid ("PGA"), poly(lactic-co-glycolic acid) ("PGLA"), or a combination thereof. In some embodiments, the CO and/or CORM is coupled to the PLA, PGA, and/or PGLA by any method known to those skilled in the art. Suitable methods for coupling the CO and/or CORM to the PLA, PGA, and/or PGLA include, for example, covalent bonding, immersing, emulsifying, impregnating, and/or engrafting the CO and/or CORM to the PLA, PGA, and/or PGLA.

The devices described herein can be any device capable of being implanted in patient. Suitable devices include, for example, vascular and cardiac occlusion devices, filters, stents, pumps, patches, catheters, prosthetics, grafts, coronary bypass circuits, plugs, valves, pacemakers, and clips.

In some embodiments, the device is a vascular stent, a vascular filter, a vascular catheter or lead, a cardiopulmonary bypass circuit, an intracardiac occlusion device, an intracardiac valve, an implantable ventricular assist device, a extracorporeal membrane oxygenation circuit, or an implantable graft at the blood interface. In various embodiments, the device is a filter, stent, pump, patch, catheter, prosthetic, graft, coronary bypass circuit, plug, valve, pacemaker, or clip.

The devices described herein can be manufactured by methods known to those skilled in the art. For example, a method of manufacturing a device described herein can include impregnating or covalently bonding with 0.01-100 micrograms of CO/CORM per mm$^2$.

Further, the device described herein can be implanted in a patient via methods known to those skilled in the art. For example, the device can be implanted by inserting a peripherally inserted central venous catheter into a vein.

Methods of Administration

The therapeutic agents described herein can be administered alone or as part of a pharmaceutically acceptable composition or formulation. In addition, the therapeutic agents can be administered all at once, at multiple times, or delivered substantially uniformly over a period of time. It is also noted that the dose of the compound can be varied over time.

The therapeutic agents described herein can be administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the therapeutic agents. The formulation can be a unit dosage containing a daily dose or unit, daily sub-dose or an appropriate fraction thereof, of the therapeutic agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the therapeutic agents is administered orally, the composition typically is in the form of a tablet, capsule, powder, solution, or elixir. When administered in tablet form, the composition additionally can contain a solid carrier, such as a gelatin or an adjuvant. For example, a tablet, capsule, and powder can comprise about 0.01% to about 95%, and preferably from about 1% to about 50%, of a CORM. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, for example, the composition can contain about 0.1% to about 90%, and preferably about 1% to about 50%, by weight, of a CORM.

When a therapeutically effective amount of the therapeutic agent is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

The therapeutic agents described herein can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the therapeutic agent to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The therapeutic agents described herein can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the therapeutic agents in water-soluble form. Additionally, suspensions of the therapeutic agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use. In some embodiments, compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The therapeutic agents described herein also can be formulated in rectal compositions, such as suppositories or retention enemas, e.g., containing conventional suppository bases. In addition to the formulations described previously, the therapeutic agents described herein also can be formulated as a depot preparation. Such long-acting formulations can be administered by implantation (for example, subcutaneously or intramuscularly) or by intramuscular injection. Thus, for example, the therapeutic agents described herein can be formulated with suitable polymeric or hydrophobic materials (for example, as an emulsion in an acceptable oil) or ion exchange resins.

Thus, the therapeutic agents described herein can be administered by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer the therapeutic agents described herein are contemplated.

In some embodiments, the therapeutic agents are administered via oral, intranasal, transbronchial and transalveolar routes via inhalation. Formulations of carriers suitable for inhalation include, but are not limited to, liquid suspensions for forming aerosols as well as powder forms for dry powder inhalation delivery systems. In one embodiment, there is no carrier but a gas is inhaled. Devices suitable for administration by inhalation of carrier formulations include, but are not limited to, atomizers, vaporizers, nebulizers, and dry powder inhalation delivery devices. In some embodiments, the therapeutic agents can be administered intranasally or by inhalation and are conveniently delivered in the form of a dry powder inhaler or an aerosol spray presentation from a pressurized container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch. Aerosol or dry powder formulations are preferably arranged so that each metered dose or "puff" delivers an appropriate dose of a compound of the invention for delivery to the patient. It will be appreciated that he overall daily dose with an aerosol will vary from patient to patient, and may be administered in a single dose or, more usually, in divided doses throughout the day.

In some cases, the therapeutic agents are administered topically. The topical formulation can include a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. Also contemplated is the use of transdermal patches, which have the added advantage of providing controlled delivery of a compound to the body. Such dosage forms are made by dissolving or dispensing the compound in the proper medium. Penetration enhancing agents can also be used to increase the flux of the compound across the skin. The rate can be controlled by either providing a rate controlling membrane or by dispersing the compound in a polymer matrix or gel. The topical formulations disclosed herein may comprise excipients. Any pharmaceutically acceptable excipient known in the art may be used to prepare topical formulations. Examples of excipients include, but are not limited to, preservatives, antioxidants, moisturizers, emollients, buffering agents, solubilizing agents, other penetration agents, skin protectants, surfactants, and propellants, and/or additional therapeutic agents used in combination to the modified particles. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In jurisdictions that forbid the patenting of methods that are practiced on the human body, the meaning of "administering" of a composition to a human subject or patient shall be restricted to prescribing a controlled substance that a human subject or patient will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

The therapeutic agents described herein can be administered to a subject at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that will be used can potentially depend on a number of factors, including the requirements of the patient or subject, the severity of the condition or disease being treated, and the pharmacological activity of the compound being administered. The determination of dosage ranges and optimal dosages for a particular patient or subject is within the ordinary skill in the art.

In various methods described herein, the CO is released from the device in an amount that is beneficial to the patient yet nontoxic. In some embodiments, the CO is administered or released from the CORM in an amount of about 1 ppm to about 1000 ppm, or about 5 ppm to about 800 ppm, or about 5 ppm to about 500 ppm, or about 10 ppm to about 250 ppm, or about 20 ppm to about 100 ppm, or about 100 ppm to about 250 ppm, or about 250 ppm to about 500 ppm or about 200 ppm to about 400 ppm, or about 100 ppm to about 300 ppm.

Mechanisms and Embodiments

Described herein are methods that produce novel, safe, and easily translatable therapeutic strategies, which can be effective to temper venous thrombo-inflammation to prevent immediate and long-term complications. Confirmation of effectiveness of these methods are shown by experiments using genetically modified mice, a novel inhalation therapeutic delivery mechanism in venous thrombosis, and complementary approaches to induce murine venous thrombosis ("VT") with IVC stasis (ligation) or flow restriction (stenosis).

In particular, the effects of HO-1 expression on innate immune activation and venous thrombus accretion were determined. In HO-1-deficient mice, venous thrombosis following DVT induction was enhanced, mediated by circulating platelet-leukocyte interaction and recruitment to the vessel wall; enhanced neutrophil activation with extracellular traps; and amplified levels of soluble pro-coagulant mediators. Further, the role of inhaled CO and/or CORM treatment in accelerating venous thrombus resolution by serving as a molecular checkpoint for vascular wall thrombo-inflammation was achieved. Inhaled CO and/or CORM treatment was found to mitigate venous thrombus formation and accelerate resolution by tempering early leukocyte-platelet interactions, neutrophil extracellular trap formation and vessel wall inflammation; and moderating levels of circulating procoagulant central to venous thrombosis.

Figure 2:
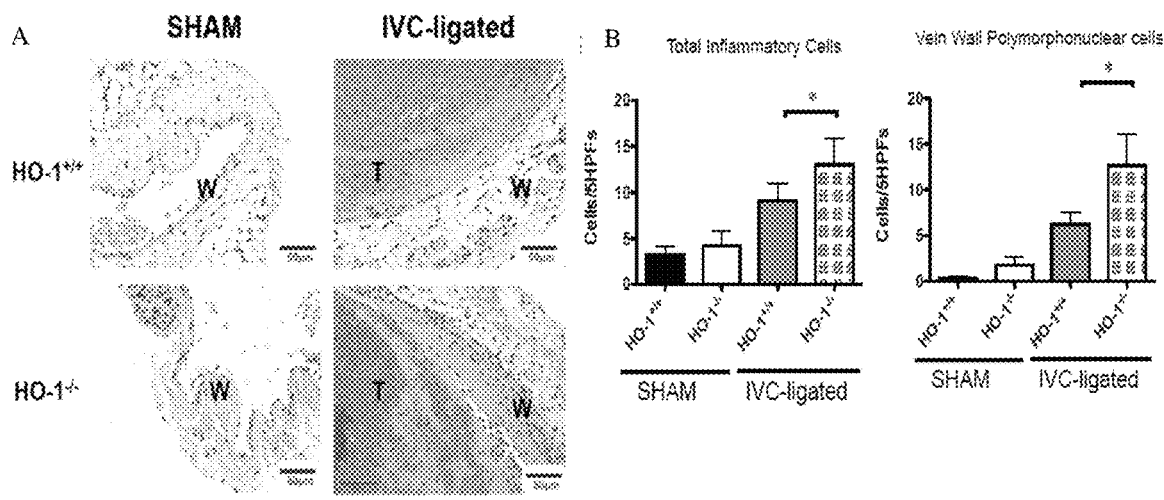
FIG. 2 depicts leukocyte recruitment to the HO-1−/−vein wall following stasis thrombosis. A. Haemotoxylin and eosin ("H&E") stain of thrombosed IVC vessel wall; B. Morphometric quantification of inflammatory cell and neutrophil recruitment to vein wall. N>3 per group. *$P<0.05$.

As vascular injury or stress may precede thrombosis, induction of HO-1 in the vessel wall can be a vital defense mechanism against venous thrombosis. Consistent with a recent study,[12] significant HO-1 induction was found in the wild-type murine vein wall in response to stasis venous thrombosis (FIG. 1A, B). However, in contrast to this study which showed no difference in thrombus size between HO-1$^{-/-}$ and controls until 10 days following surgery, data show a significant increase in thrombus size and weight as early as two days following complete IVC ligation (FIG. 1C, D). To investigate the clinical spectrum of venous thrombosis, established models of IVC ligation (stasis) and "flow restriction" (stenosis) were used to induce venous thrombosis in the laboratory.[5,6,46] Thrombus size in wild-type mice peaks at two days following IVC ligation (FIG. 1B). Additional preliminary data include histomorphometric analysis at this early time point demonstrating an increase in leukocyte infiltration into the vessel wall, driven by a wave of neutrophil recruitment (FIG. 2A-C). Analysis of sham surgical controls showed no significant difference between venous leukocyte infiltration between HO-1$^{-/-}$ mice and controls, confirming validity of the comparison following VT.

Circulating leukocyte-platelet interactions following VT induction was investigated by establishing a novel, multi-color flow cytometry protocol using whole blood. Heterotypic hematopoietic cell interactions are potent effectors of inflammation in venous thrombogenesis.[8] A multi-color flow cytometry protocol facilitates evaluation of circulating cell interactions in whole blood following VT induction. This protocol demonstrates feasibility of whole blood flow cytometry for evaluation of circulating granulocyte-platelet and monocyte-leukocyte interactions. Citrated whole blood undergoes RBC lysis, following by labeling with DAPI and antibodies targeting CD45, CD11b, Ly6C, Ly6G, CD41, CD62P. Live cells are gated and further subgated by CD45 (lymphocyte) and Ly6G (neutrophil) or CD11 b/Ly6C (monocyte) to identify the leukocyte subset, then analyzed for adherent platelet CD41+CD62P+ expression.

Figure 3:
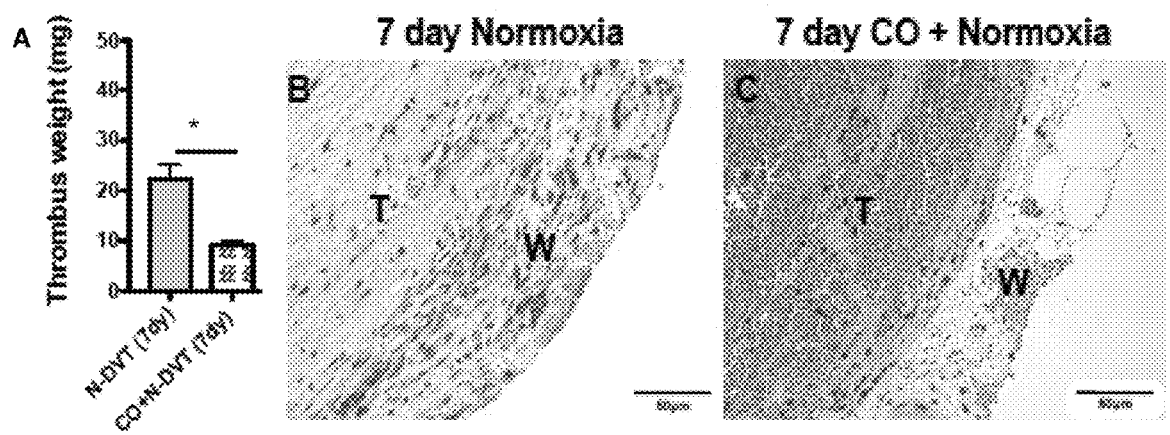
FIG. 3 demonstrates that inhaled CO can be a potential therapeutic in venous thrombosis. Venous stasis thrombus burden (A) and vessel wall leukocyte infiltration (B, C) are reduced after 7 d treatment with inhaled CO after IVC ligation. "N"=normoxia, N=4-11/group, *$P<0.05$.

Carbon monoxide was focused on for these studies because it is an end product from heme degradation by HO-1. It was previously found that chronic treatment with inhaled carbon monoxide has potent effects, rescuing lungs from ischemic injury.[18,19] In these studies, CO inhibited the induction of Egr-1 by physiologic stress and in turn, abrogated expression of Egr-1 downstream coagulopathic target genes including tissue factor, serpine-1, interleukin-1, and TNF-alpha.[19] This lends further support that inhaled CO can temper thrombo-inflammation in venous thrombosis. More recently, it was observed that chronic exposure to low dose inhaled carbon monoxide reduced pulmonary neutrophil and monocyte recruitment.[17] Data using long-term, inhaled carbon monoxide (7 days, 250 ppm for 1 hour twice daily) and normoxia-treated controls, revealed a profound reduction in chronic thrombus burden and leukocyte infiltration into the vessel wall with 7 days CO treatment following venous stasis thrombosis (FIG. 3A-C).

To determine whether carbon monoxide-releasing molecules can be used as a therapeutic in prevention of flow-restriction mediated venous thrombosis (a model of venous thrombosis that mimics human venous clot, unlike IVC ligation), mice were injected with CORM-3 (Sigma SML0496, 10 mg/kg intraperitoneal injection) and subjected to IVC flow-restriction to induce thrombosis. Remarkably, CORM-3 treated mice developed no venous thrombus (0%, n=5) compared with controls (48%, n=21. P=0.001).

EXAMPLES

Example 1: Determination of the Effects of HO-1 Expression on Innate Immune Activation and Venous Thrombus Accretion The effect of HO-1 depletion on venous thrombus under conditions of venous stasis and stenosis (flow restriction) was determined.

Figure 4:
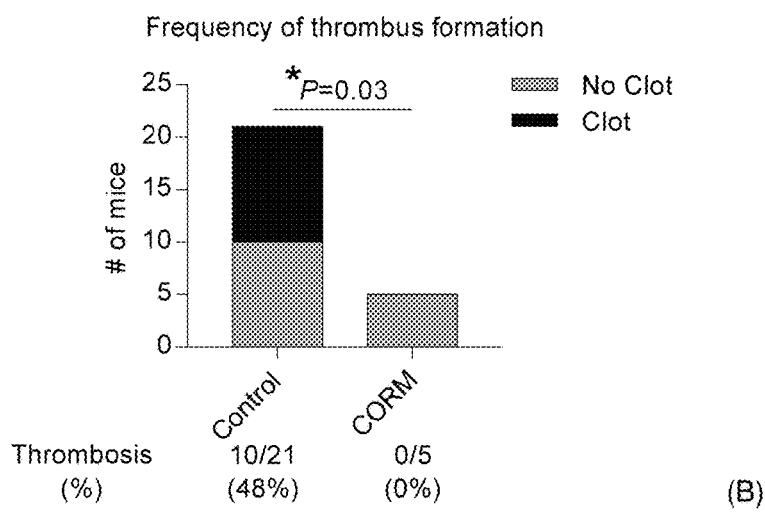
FIG. 4 demonstrates that CORM-3 treatment prevents venous thrombosis. (A) C57B/6J mice treated with CORM-3 were protected from venous thrombus compared with controls, following VT induction by IVC flow-restriction which induces thrombus similar to human venous thrombus. (B) Frequency of clot was 0% in CORM-3 treated mice, compared with 48% in control mice (right). N=5-21, left: P=0.001 using Student's t test. Right: P=0.03 using Fisher's exact test.
Figure 4:
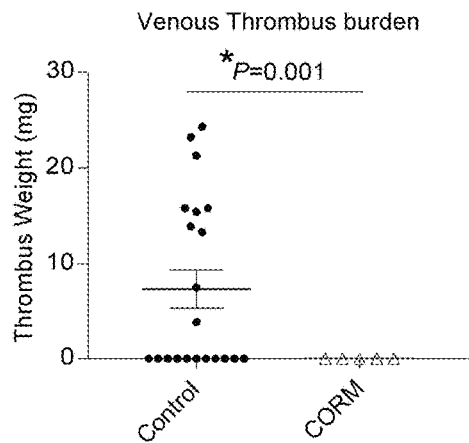
Figure 5:
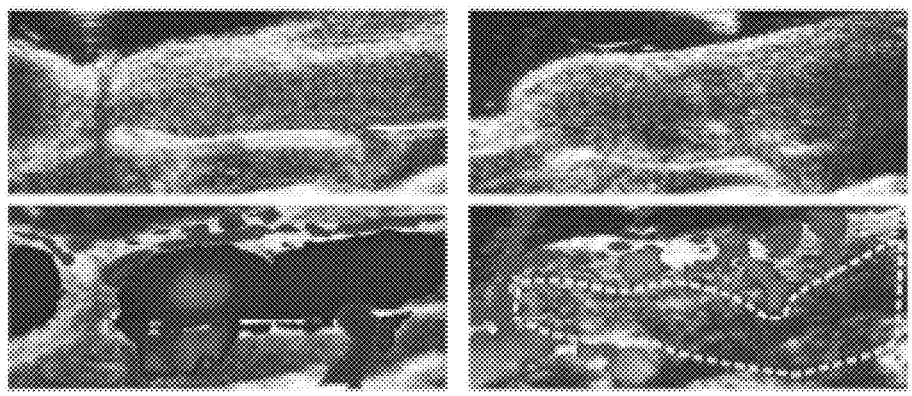
FIG. 5 depicts murine IVC stenosis using a 0.31 mm (30 gauge) external diameter flow restriction model. IVC stenosis shown in B-mode ultrasound (upper panels) and with color Doppler (lower panels). Flow is visible in the infrarenal IVC immediately post IVC stenosis (left) and limited flow with thrombus formation (yellow outline, right) 2 d after surgery.[5]

To determine the time course of venous thrombus formation, mice aged 8-10 weeks deficient in HO-1 (HO-1$^{-/-}$) undergo venous stasis (complete IVC ligation & occlusion). While a prior study showed no difference in thrombus burden until 10 days in HO-1$^{-/-}$ mice, data demonstrates a marked increase in thrombus size early (2 days) following IVC ligation (FIG. 1C, D). Thrombus burden is quantified by ultrasound as previously done (FIG. 4)[5], and measuring total IVC+thrombus weight en toto. Thrombus is separated from IVC, prior to measuring length and mass. While prior studies have shown peak thrombus burden to occur at 2 days, it is possible that coagulation remains unconstrained in HO-1$^{-/-}$ mice for a longer period. A temporal pattern of thrombus formation is established in WT and HO-1$^{-/-}$ mice at 1, 2, 7, 10 days following thrombus induction. This also sheds further light on the contradistinction observed between data and a previous report suggesting no difference in 2d thrombus size.[12] As complete stasis (IVC ligation) does not reflect the complete spectrum of clinical venous thrombosis, these experiments also are performed in another, clinically relevant model of flow restriction.[5] This allows one to distinguish the effects of complete blood stasis and hypoxia in a model of IVC ligation, from effects of restricted and turbulent flow with continued recruitment of intravascular leukocytes and platelets in propagation of clot following thrombus initiation (FIG. 5).

Figure 6:
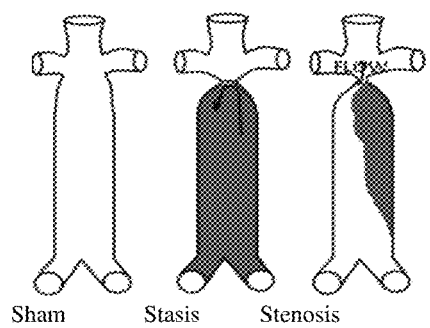
FIG. 6 depicts murine models of venous thrombosis with stasis and flow restriction.

Example 2: Defining the Role of Carbon Monoxide Therapy to Accelerate Venous Thrombus Resolution by Serving as a Molecular Checkpoint for Vascular Wall Thrombo-Inflammation The effect of CO on large vein thrombogenesis was determined. WT mice undergo venous thrombus induction by stasis or stenosis, followed by exposure to inhaled CO (250 ppm) for one hour twice daily. Data show a robust reduction in thrombus frequency with CORM treatment, and thrombus size at 7 days with CO exposure. Thrombus burden was assessed as in SA1 indirectly (ultrasound, FIG. 6) and directly (thrombus weight/length), at pre-determined time points after surgery (1 d, 2 d, 7 d, 10 d, 21 d).

Also, it was determined that CO exposure (inhaled CO or CORM) induces heme oxygenase-1 expression in sham-operated WT IVC compared with normoxic controls by quantitative RT-PCR and immunoblotting. Therefore, inhaled CO can trigger a venous anti-inflammatory and anti-thrombotic program. Also, whether CO or CORM treatment alone is sufficient to rescue HO-1$^{-/-}$ mice from exaggerated early venous thrombosis was assessed. HO-1$^{-/-}$ mice undergo venous stasis or stenosis thrombus induction, followed by CORM or inhaled CO treatment. Thrombus size was measured at the time of expected peak thrombus burden.

Example 3: Determination of Whether CO and/or CORM Treatment Temper the Innate Immune Response Circulating heterotypic inter-cellular associations in WT mice using whole blood flow cytometry was examined as previously described. WT mice undergo IVC stasis or stenosis followed by exposure to CORM, inhaled CO or normoxia. As CO is known to reduce activation of platelets and neutrophils, and promotes macrophage phenotype switching,[24,50,51] inhaled CORM and/or CO treatment mitigate these heterotypic cellular interactions. Given that platelet-neutrophil interactions are likely to play a role in early thrombogenesis, these relationships were examined at day 1 and 2 following IVC surgery.

Whether CORM and/or CO treatment can modify the natural history of platelet-leukocyte interactions in HO-1$^{-/-}$ mice with induced venous thrombosis also was determined.

The effect of CORM and/or CO on neutrophil activation and extracellular trap release also was quantified. Plasma from thrombus-induced mice was used to quantify cfDNA and analyzed based on CORM/CO exposure. Histologic thrombus sections was probed for extracellular DNA and H3-cit and quantified.

Example 4: Determination of Whether CORM and/or Inhaled CO have Systemic Effects on Soluble Pro-Cogulant Molecules Whether CORM and/or CO treatment decreases the induction of circulating pro-coagulant molecules was evaluated by measuring plasma levels of VWF, P-selectin, and tissue factor, which have been strongly implicated in VT formation and propagation. Paraffin-embedded thrombus sections was probed and analyzed immunohistologically for fibrin expression.

Alternative Approaches

Later time points to evaluate thrombus resolution were also assessed. HO-1 deficient mice are known to present challenges in breeding. Also, a flow restriction model of thrombus induction was used.[5] Without being bound by any particular theory, heterotypic cell interactions and activation propagate exaggerate venous thrombosis. This statement is based on studies demonstrating the role of HO-1 in maintaining vital homeostatic functions in each implicated cell type.[11,28,52]

The contribution of specific cell-types to thrombogenesis by platelet or neutrophil depletion and adoptive transfer experiments also was examined.[6] Additional priming of the neutrophil and platelets was examined in vitro, using thrombin-activated platelets to prime neutrophils in co-culture studies to examine histone "studding" on liberated extracellular nucleic acids. Other experiments consider treatment with intravenous DNase to determine if multiple mechanisms contribute to thrombosis in these mice. Whole blood cytometry evaluates circulating cell interactions. A new technique for vein wall flow cytometry was developed. In this method, the vein wall can be minced and digested, and purified cell populations were able to be quantified by flow cytometry with pooled samples. Also, confocal microscopy was be used to enable direct immuno-colocalization, using different fluorophores conjugated to the cell marker of interest.

Changes in venous thrombosis size at early and later time points with inhaled CO treatment occurs. In some cases, the treatment dose is subtherapeutic. The dose up to 500 ppm is titrated, which has been studied and found to be safe in clinical trials.[53] Pre-conditioning with CO prior to stasis thrombosis also was considered. Monocyte/macrophage polarization in the thrombus and vessel wall by complementary flow cytometry and confocal microscopy also was accomplished. Findings are further investigated using specific inducers and inhibitors of macrophage polarization[56] or using a bone marrow transplant model.[54] While the bioavailability of inhaled CO in the IVC at the thrombus-vessel wall interface remains unknown, significant effects have been noted. Synthetic carbon monoxide-releasing molecules (CORM) have been utilized in vitro and in vivo to induce CO.[55,56] Of the water-soluble CORMs which can be given by intraperitoneal or intravenous injection for more reliable delivery, CORM-3 has shown potent effects on inflammation in pre-clinical studies.[56] Additional CORM candidate molecules were tested for their effects in reducing venous thrombosis and/or inflammation. The role of the pro-oxidant molecule heme in VT also was examined. Experiments with exogenous heme-sequestering agents including hemopexin, factor IX, XII and XIII shed further light on whether the protection from VT by HO-1 was attributed solely to CO production or multifactorial.

The role of heme oxygenase-1 in venous thrombogenesis is more defined, and the cellular interactions and soluble procoagulants driving exaggerated thrombosis in HO-1$^{-/-}$ mice was dissected. The role of CORM and/or inhaled carbon monoxide as a novel therapeutic is defined in suppressing the inflammatory and procoagulant response to induced venous thrombosis.

Materials and Methods C57B/6 (wild-type) mice were purchased from the Jackson Laboratory (000664), HO-1$^{-/-}$ mice (provided by Dr. Arthur Mu-En Lee, active colony backbred on a C57B/6J background for >20 generations) at 8-12 weeks were utilized.

Rodent Models:

Stasis thrombosis model: Total IVC Ligation Model of Venous Thrombosis (FIG. 5)

The mouse makes an excellent animal model of stasis-induced venous thrombosis. Mice, weighing 20 to 30 g, were anesthetized with an inhalation mixture of isoflurane gas (1.5% to 2%) and oxygen (100%), placed in dorsal recumbency and aseptically prepped for surgery. A midline laparotomy was made, the small bowel was exteriorized from the body cavity and moved slightly to the left of the animal, and then the IVC was directly approached by careful blunt dissection. Blunt dissection was facilitated using a sterile applicator swab and extra delicate half curved tissue forceps. Care was taken in handling mouse tissue due to its fragility. Periodically, the exteriorized bowel was moistened with sterile saline to prevent its desiccation. For consistent thrombus formation (90 to 95%), ligation of the IVC with a 7-0 prolene below the renal veins, ligation of an occasional side venous branch and cauterization of a deep posterior branch was performed if indicated to account for normal variation in anatomy. The laparotomy incision was closed in a 2-layer fashion using a 5-0 nonreactive suture material and VetBond glue (3M). Harvest of the IVC was performed at pre-determined time points.

"Flow restriction" (Stenosis) thrombosis model: Partial IVC stenosis Model of Venous Thrombosis (FIG. 5) This model is a "flow-restriction" (or "stenosis) model in which the lumen is reduced by ~90%. This model invokes disturbed flow at the stenosis site as a model for turbulent flow in venous valve pockets, where thrombi frequently develop. It also has applications to human venous "impingement" conditions, such as May Thurner syndrome. Mice, weighing 20 to 30 g, were anesthetized using an inhalation mixture of isoflurane gas (1.5%-2%) and oxygen (100%), placed in dorsal recumbence, and the IVC was approached directly via a midline laparotomy utilizing aseptic technique. A 7-0 Prolene suture (Ethicon, Inc. Somerville, NJ) was fastened around the IVC over a blunted 30-gauge needle (which serves as a spacer). After removal of the spacer, the abdomen was closed, and the mouse was allowed to recover. This procedure is referred to as the "stenosis" or "flow restriction" model. Sham procedures followed the same protocol except the ligature were passed under the IVC and then removed from the mouse without fastening. Mice were humanely euthanized and thrombus formation assessed 2-7 days after laparotomy.

Inhaled Carbon monoxide exposure: Mice were randomly assigned to the normoxia or carbon monoxide exposure group prior to IVC ligation or stenosis surgery. The carbon monoxide group was exposed to 250 ppm CO at a flow rate of 10 L/min for 1 h twice daily. One cohort of mice received "pre-conditioning" with CO exposure 1 day prior to surgery. To achieve 75% $O_2$, 100% $O_2$ is delivered at a flow rate of 0.5 l/min into a custom-made 1.5-m$^3$ plastic chamber. Oxygen concentrations were monitored continuously with an oxygen analyzer (Neutronics, Exton, PA), gas lines were filtered with activated charcoal to remove excess ammonia, and calcium chloride used to maintain $CO_2$ levels below 0.05%. A CO analyzer (Ntron model 1100; Neutronics, Exton, PA) were used to monitor CO levels continuously in the chamber.

Ultrasound: Mice were anesthetized using isoflurane as above, and Doppler ultrasonography performed as previously described.[5]

Statistical Analysis for SA1 and SA2:

Experimental numbers are based on published literature. Data was analyzed using Graph Pad Prizm software (La Jolla, CA) and appropriate statistical methods, including two-tailed Student's t-test and ANOVA. Pvalues<0.005 were assigned significance. For example, to compare thrombus size between groups, published work has shown ~10-20% change between groups. Considering alpha of 0.05, and power of 80%, N>12 is necessary. For flow cytometry assays, observed ~25% differences are observed, and N>7 is sufficient. In vitro experiments using primary cells was performed for a minimum of N=5 biological replicates and triple technical replicates.

Immunohistochemical/immunofluorescent imaging was semi-quantitatively measured using ImageJ software (NIH). Additional assays including ELISAs were performed per manufacturer protocols and analyzed as above.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step not specifically disclosed.

The practice of a method disclosed herein, and individual steps thereof, can be performed manually and/or with the aid of or automation provided by electronic equipment.

Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference.

REFERENCES

1. Wakefield T W, McLafferty R B, Lohr J M, et al. Call to action to prevent venous thromboembolism. Journal of vascular surgery 2009; 49:1620-3.

2. Barnes G D, . . . Kanthi, Y., Wakefield, T. W. Venous thromboembolism: diagnosis, treatment and the prevention of long-term complications. Rev Vasc Med 2014; 2:136-42.

3. Barnes G D, Kanthi, Y., Froehlich, J. B. Venous thromboembolism: predicting recurrence and the need for extended anticoagulation. Vasc Med 2015; 20:143-52.

4. Byrnes J R, Duval C, Wang Y, et al. Factor XIIIa-dependent retention of red blood cells in clots is mediated by fibrin alpha-chain crosslinking. Blood 2015; 126:1940-8.

5. Meng H, Yalarvarthi S, Kanthi Y. et al. In vivo role of neutrophil extracellular traps in antiphospholipid antibody-mediated venous thrombosis. Arthritis and Rheumatology 2016; (accepted, in press).

6. Obi A T, Andraska E, Kanthi Y, et al. Gram negative pneumonia alters large vein cellular adhesion molecule profile and potentiates experimental stasis venous thrombosis. Journal of Vascular Research 2016; (accepted, in press).

7. Saha P, Humphries J, Modarai B, et al. Leukocytes and the natural history of deep vein thrombosis: current concepts and future directions. Arteriosclerosis, thrombosis, and vascular biology 2011; 31:506-12.

8. von Bruhl M L, Stark K, Steinhart A, et al. Monocytes, neutrophils, and platelets cooperate to initiate and propagate venous thrombosis in mice in vivo. The Journal of experimental medicine 2012; 209:819-35.

9. Chen B, Guo L, Fan C, et al. Carbon monoxide rescues heme oxygenase-1-deficient mice from arterial thrombosis in allogeneic aortic transplantation. The American journal of pathology 2009; 175:422-9.

10. Cheng C, Noordeloos A M, Jeney V, et al. Heme oxygenase 1 determines atherosclerotic lesion progression into a vulnerable plaque. Circulation 2009; 119:3017-27.

11. Wenzel P, Rossmann H, Muller C, et al. Heme oxygenase-1 suppresses a pro-inflammatory phenotype in monocytes and determines endothelial function and arterial hypertension in mice and humans. European heart journal 2015; 36:3437-46.

12. Tracz M J, Juncos J P, Grande J P, et al. Induction of heme oxygenase-1 is a beneficial response in a murine model of venous thrombosis. The American journal of pathology 2008; 173:1882-90.

13. Lindenblatt N, Bordel R, Schareck W, Menger M D, Vollmar B. Vascular heme oxygenase-1 induction suppresses microvascular thrombus formation in vivo. Arteriosclerosis, thrombosis, and vascular biology 2004; 24:601-6.

14. True A L, Olive M, Boehm M, et al. Heme oxygenase-1 deficiency accelerates formation of arterial thrombosis through oxidative damage to the endothelium, which is rescued by inhaled carbon monoxide. Circulation research 2007; 101:893-901.

15. Bean C J, Boulet S L, Ellingsen D, et al. Increased risk of venous thromboembolism is associated with genetic variation in heme oxygenase-1 in Blacks. Thrombosis research 2012; 130:942-7.

16. Mustafa S, Weltermann A, Fritsche R, et al. Genetic variation in heme oxygenase 1 (HMOX1) and the risk of recurrent venous thromboembolism. Journal of vascular surgery 2008; 47:566-70.

17. Anyanwu A C, Bentley J K, Popova A P, et al. Suppression of inflammatory cell trafficking and alveolar simplification by the heme oxygenase-1 product carbon monoxide. American journal of physiology Lung cellular and molecular physiology 2014; 306:L749-63.

18. Fujita T, Toda K, Karimova A, et al. Paradoxical rescue from ischemic lung injury by inhaled carbon monoxide driven by derepression of fibrinolysis. Nature medicine 2001; 7:598-604.

19. Mishra S, Fujita T, Lama V N, et al. Carbon monoxide rescues ischemic lungs by interrupting MAPK-driven expression of early growth response 1 gene and its downstream target genes. Proceedings of the National Academy of Sciences of the United States of America 2006; 103:5191-6.

20. Izumi M, Migita K, Nakamura M, et al. Risk of venous thromboembolism after total knee arthroplasty in patients with rheumatoid arthritis. The Journal of rheumatology 2015; 42:928-34.

21. Aksu K, Donmez A, Keser G. Inflammation-induced thrombosis: mechanisms, disease associations and management. Current pharmaceutical design 2012; 18:1478-93.

22. Esmon C T. Inflammation and thrombosis. Journal of thrombosis and haemostasis: JTH 2003; 1:1343-8.

23. Ridker P M, Danielson E, Fonseca F A, et al. Rosuvastatin to prevent vascular events in men and women with elevated C-reactive protein. The New England journal of medicine 2008; 359:2195-207.

24. Brune B, Ullrich V. Inhibition of platelet aggregation by carbon monoxide is mediated by activation of guanylate cyclase. Molecular pharmacology 1987; 32:497-504.

25. Otterbein L, Chin B Y, Otterbein S L, Lowe V C, Fessler H E, Choi A M. Mechanism of hemoglobin-induced protection against endotoxemia in rats: a ferritin-independent pathway. The American journal of physiology 1997; 272:L268-75.

26. Otterbein L, Sylvester S L, Choi A M. Hemoglobin provides protection against lethal endotoxemia in rats: the role of heme oxygenase-1. American journal of respiratory cell and molecular biology 1995; 13:595-601.

27. Wiesel P, Patel A P, DiFonzo N, et al. Endotoxin-induced mortality is related to increased oxidative stress and end-organ dysfunction, not refractory hypotension, in heme oxygenase-1-deficient mice. Circulation 2000; 102:3015-22.

28. Chiang N, Shinohara M, Dalli J, et al. Inhaled carbon monoxide accelerates resolution of inflammation via unique proresolving mediator-heme oxygenase-1 circuits. Journal of immunology 2013; 190:6378-88.

29. Diaz J A, Shaydakov M E, Chatterjee A, et al. Resolvin D2 reduces thrombus burden and attenuates inflammatory signaling pathways in a murine model of venous thrombosis. Arteriosclerosis, thrombosis, and vascular biology 2015; 35.

30. Suffredini A F. National Institutes of Health Clinical Center. Carbon monoxide to prevent lung inflammation. https://clinicaltrialsgov/ct2/show/NCT00094406 NLM Identifier NCT00094406 2004 [cited 2016 Sep. 20].

31. Machado R. University of Illinois at Chicago. Carbon Monoxide therapy for severe pulmonary arterial hypertension. https://clinicaltrialsgov/ct2/show/NCT01523548 NLM Identifier NCT01523548 2012 [cited 2016 Sep. 20].

32. Kerstjens H A. Groningen Research Institute for Asthma and COPD. Modification of chronic inflammation by inhaled carbon monoxide in patients with stable COPD. https://clinicaltrialsgov/ct2/show/NCT00122694 NLM Identifier NCT00122694 2006 [cited 2016 Sep. 20].

33. Bathoorn E, Slebos D J, Postma D S, et al. Anti-inflammatory effects of inhaled carbon monoxide in patients with COPD: a pilot study. The European respiratory journal 2007; 30:1131-7.

34. Resch H, Zawinka C, Weigert G, Schmetterer L, Garhofer G. Inhaled carbon monoxide increases retinal and choroidal blood flow in healthy humans. Investigative ophthalmology & visual science 2005; 46:4275-80.

35. Choi AMK. Weil Medical College of Cornell University. Safety Study of Inhaled Carbon Monoxide to Treat Acute Respiratory Distress Syndrome (ARDS). http://clinicaltrialsgov/NCT02425579 NLM Identifier: NCT02425579 2015 [cited 2016 Sep. 20].

36. Wang C. Daping Hospital and the Research Institute of Surgery of the Third Military Medical University. Safety and adverse reaction study of neonatal to inhaled carbon monoxide. https://clinicaltrialsgov/ct2/show/NCT01818843 NLM Identifier: NCT01818843 2013 [cited 2016 Sep. 20].

37. Grosse S D, Nelson R E, Nyarko K A, Richardson L C, Raskob G E. The economic burden of incident venous thromboembolism in the United States: A review of estimated attributable healthcare costs. Thrombosis research 2016; 137:3-10.

38. Kahn S R, Elman E A, Bomais C, Blostein M, Wells P S. Post-thrombotic syndrome, functional disability and quality of life after upper extremity deep venous thrombosis in adults. Thrombosis and haemostasis 2005; 93:499-502.

39. Evans C E, Humphries J, Waltham M, et al. Upregulation of hypoxia-inducible factor 1 alpha in local vein wall is associated with enhanced venous thrombus resolution. Thrombosis research 2011; 128:346-51.

40. Brill A, Suidan G L, Wagner D D. Hypoxia, such as encountered at high altitude, promotes deep vein thrombosis in mice. Journal of thrombosis and haemostasis: JTH 2013; 11:1773-5.

41. McInturff A M, Cody M J, Elliott E A, et al. Mammalian target of rapamycin regulates neutrophil extracellular trap formation via induction of hypoxia-inducible factor 1 alpha. Blood 2012; 120:3118-25.

42. Li Y D, Ye B Q, Zheng S X, et al. NF-kappaB transcription factor p50 critically regulates tissue factor in deep vein thrombosis. The Journal of biological chemistry 2009; 284:4473-83.

43. Geddings J E, Hisada Y, Boulaftali Y, et al. Tissue factor-positive tumor microvesicles activate platelets and enhance thrombosis in mice. Journal of thrombosis and haemostasis: JTH 2016; 14:153-66.

44. Diaz J A, Fuchs T A, Jackson T O, et al. Plasma DNA is Elevated in Patients with Deep Vein Thrombosis. Journal of vascular surgery Venous and lymphatic disorders 2013; 1.

45. Chou J, Mackman N, Merrill-Skoloff G, Pedersen B, Furie B C, Furie B. Hematopoietic cell-derived microparticle tissue factor contributes to fibrin formation during thrombus propagation. Blood 2004; 104:3190-7.

46. Diaz J A, Obi A T, Myers D D, Jr., et al. Critical review of mouse models of venous thrombosis. Arteriosclerosis, thrombosis, and vascular biology 2012; 32:556-62.

47. Etulain J, Martinod K, Wong S L, Cifuni S M, Schattner M, Wagner D D. P-selectin promotes neutrophil extracellular trap formation in mice. Blood 2015; 126:242-6.

48. Villanueva E, Yalavarthi S, Berthier C C, et al. Netting neutrophils induce endothelial damage, infiltrate tissues, and expose immunostimulatory molecules in systemic lupus erythematosus. Journal of immunology 2011; 187:538-52.

49. Desch K C, Ozel A B, Siemieniak D, et al. Linkage analysis identifies a locus for plasma von Willebrand factor undetected by genome-wide association. Proceedings of the National Academy of Sciences of the United States of America 2013; 110:588-93.

50. Weis N, Weigert A, von Knethen A, Brune B. Heme oxygenase-1 contributes to an alternative macrophage activation profile induced by apoptotic cell supernatants. Molecular biology of the cell 2009; 20:1280-8.

51. Morse D, Choi A M. Inhaled CO in the treatment of acute lung injury. American journal of physiology Lung cellular and molecular physiology 2008; 294:L642-3.

52. Peng L, Mundada L, Stomel J M, et al. Induction of heme oxygenase-1 expression inhibits platelet-dependent thrombosis. Antioxidants & redox signaling 2004; 6:729-35.

53. Mayr F B, Spiel A, Leitner J, et al. Effects of carbon monoxide inhalation during experimental endotoxemia in humans. American journal of respiratory and critical care medicine 2005; 171:354-60.

54. Hyman M C, Petrovic-Djergovic D, Visovatti S H, et al. Self-regulation of inflammatory cell trafficking in mice by the leukocyte surface apyrase CD39. The Journal of clinical investigation 2009; 119:1136-49.

55. Urquhart P, Rosignoli G, Cooper D, Motterlini R, Perretti M. Carbon monoxide-releasing molecules modulate leukocyte-endothelial interactions under flow. The Journal of pharmacology and experimental therapeutics 2007; 321: 656-62.

56. Ferrandiz M L, Maicas N, Garcia-Amandis I, et al. Treatment with a CO-releasing molecule (CORM-3) reduces joint inflammation and erosion in murine collagen-induced arthritis. Annals of the rheumatic diseases 2008; 67:1211-7.

57. Kramkowski et al., Arterioscler Thromb Vasc Biol 32(9):2149-57 (2012).

58. Chung et al., J Epidemiol Community Health 69:557-562 (2015).

59. Hayashi et al., Eur J Physiol 456:1239-1251 (2008).

60. Motterlini et al., Medicinal Gas Research 2(28):1-12 (2012).

61. Soni et al., Thrombosis Research 127:551-559 (2011).

62. Burgaud et al., Current Pharmaceutical Design, 8(3): 201-213(13) (2002)

63. Gomperts et al., Am J Hematol. 92(6):569-582 (2017).

We claim:

1. An implantable device comprising a surface covalently bound to: (i) carbon monoxide ("CO"), (ii) a carbon monoxide releasing molecule ("CORM") or a pharmaceutically acceptable salt thereof, or (iii) both CO and a CORM or a pharmaceutically acceptable salt thereof, wherein the implantable device is configured to release CO in an amount of about 100 ppm to about 300 ppm.

2. The implantable device of claim 1, wherein the device is a vascular stent, a vascular filter, a vascular catheter or lead, a cardiopulmonary bypass circuit, an intracardiac occlusion device, an intracardiac valve, an implantable ventricular assist device, a extracorporeal membrane oxygenation circuit, or an implantable graft at the blood interface.

3. The implantable device of claim 1, wherein the surface comprises polylactic acid ("PLA"), polyglycolic acid ("PGA"), poly(lactic-co-glycolic acid) ("PGLA"), or a combination thereof.

4. The implantable device of claim 1, wherein the CORM is selected from the group consisting of tricarbonyldichlororuthenium (II) dimer ("CORM-2"), tricarbonylchloro(glycinato)ruthenium (II) ("CORM-3"), [Me$_4$N][Mn(CO)$_4$(thioacetate)$_2$]("CORM-371"), dimanganese decacarbonyl, iron pentacarbonyl, and a combination thereof.

5. The device of claim 4, wherein the CORM is CORM-3.

6. The device of claim 1, wherein the CORM is a selected from the group consisting of dichloromethane, sodium boranocarbonate ("CORM-A1"), and a combination thereof.

7. The device of claim 1, wherein the CORM is coupled to a targeted delivery vector.

8. A method of inhibiting leukocyte recruitment to a vessel wall for treating a physiological venous thrombosis in a patient suffering a disease or condition associated with low or no blood flow, sickle cell disease, or a combination thereof, in a patient in need thereof comprising:
   (a) administering to the patient (i) CO, (ii) a CORM or pharmaceutically acceptable salt thereof, or (iii) both CO and a CORM or a pharmaceutically acceptable salt thereof in an amount sufficient to administer or release CO in an amount of about 100 ppm to about 300 ppm; wherein the disease or condition is selected from primary or recurrent venous thrombophlebitis, arteriovenous shunt failure, stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation, atrial fibrillation, atrial flutter-related thrombus, endovascular heat-induced thrombus, valve thrombosis, catheter thrombosis, thrombosis associated with tissue ablation procedures, implantable lead-associated thrombosis, and a combination thereof; or
   (b) implanting the device of claim 1 in the patient.

9. The method of claim 8, wherein the device of claim 1 is implanted in the patient and the patient suffers from a disease or condition selected from venous thromboembolism ("VTE"), native or artificial thrombosis, primary or recurrent thrombophlebitis, arteriovenous shunt failure, stroke, myocardial infarction, transient ischemic attack, aortic thrombosis, limb vascular thrombus, limb ischemia, mesenteric vessel thrombus, cerebral venous thrombus, cancer-associated thrombus, venous stent thrombosis, arterial stent thrombosis, vascular inflammation, atrial fibrillation, atrial flutter-related thrombus, endovascular heat-induced thrombus, valve thrombosis, catheter thrombosis, thrombosis associated with tissue ablation procedures, implantable lead-associated thrombosis, and a combination thereof.

10. The method of claim 8, further comprising administering to the patient one or more therapeutic agents.

11. The method of claim 10, wherein the one or more therapeutic agents comprises carbon monoxide, nitric oxide or a compound that releases nitric oxide, oxygen, an anticoagulant, an anti-inflammatory agent, a protease activated receptor ("PAR") inhibitor, a thienopyridine, a lipoxygenase-derived platelet inhibitor, a cell adhesion molecule inhibitor, or combinations thereof;
   optionally wherein the compound that releases nitric oxide selected from the group consisting of SIN-1, NCX-4016, NCX-701, nitroglycerin, sodium nitroprusside, and a combination thereof;
   optionally wherein the anticoagulant is selected from the group consisting of a coumarin, an indandione, a factor Xa inhibitor, factor XI inhibitor, factor XII inhibitor, factor XIII inhibitor, a heparin, a thrombin inhibitor, and a combination thereof;
   optionally wherein the factor Xa inhibitor is fondaparinux, rivaroxaban, apixaban, edoxaban, otamixaban, letaxaban, eribaxaban, darexaban, or a combination thereof;
   optionally wherein the heparin is dalteparin, tinzaparin, enoxaparin, heparin, danaparoid, or a combination thereof; and
   optionally wherein the thrombin inhibitor is bivalirudin, dabigatran, argatroban, desirudin, lepirudin, or combinations thereof.

* * * * *

UNITED STATES PATENT AND TRADEMARK OFFICE
CERTIFICATE OF CORRECTION

PATENT NO. : 12,029,755 B2
APPLICATION NO. : 17/535080
DATED : July 9, 2024
INVENTOR(S) : Yogendra Kanthi et al.

Page 1 of 1

It is certified that error appears in the above-identified patent and that said Letters Patent is hereby corrected as shown below:

In the Claims

At Column 25, Line 58, "a selected" should be -- selected --.

Signed and Sealed this
Fourth Day of February, 2025

Coke Morgan Stewart
*Acting Director of the United States Patent and Trademark Office*